United States Patent
Stehno-Bittel et al.

(10) Patent No.: US 9,567,570 B2
(45) Date of Patent: Feb. 14, 2017

(54) ASSAYS USING A MULTI-DIVOT PLATFORM AND MULTI-SOURCE, MULTI-CELL TYPE CLUSTERS

(71) Applicant: The University of Kansas, Lawrence, KS (US)

(72) Inventors: Lisa Stehno-Bittel, Bonner Springs, KS (US); Karthik Ramachandran, Kansas City, KS (US); Sonia Rawal, Lenexa, KS (US)

(73) Assignee: The University of Kansas, Lawrence, KS (US)

( * ) Notice: Subject to any disclaimer, the term of this patent is extended or adjusted under 35 U.S.C. 154(b) by 0 days.

(21) Appl. No.: 14/436,041

(22) PCT Filed: Oct. 11, 2013

(86) PCT No.: PCT/US2013/064583
§ 371 (c)(1),
(2) Date: Apr. 15, 2015

(87) PCT Pub. No.: WO2014/062505
PCT Pub. Date: Apr. 24, 2014

(65) Prior Publication Data
US 2015/0259650 A1    Sep. 17, 2015

Related U.S. Application Data

(60) Provisional application No. 61/715,570, filed on Oct. 18, 2012.

(51) Int. Cl.
| | |
|---|---|
| *C12N 5/077* | (2010.01) |
| *A61K 35/39* | (2015.01) |
| *C12N 5/071* | (2010.01) |
| *A01N 1/02* | (2006.01) |
| *G01N 33/50* | (2006.01) |
| *G01N 33/543* | (2006.01) |
| *A61K 35/28* | (2015.01) |
| *G01N 33/74* | (2006.01) |

(52) U.S. Cl.
CPC .......... *C12N 5/0677* (2013.01); *A01N 1/0284* (2013.01); *A61K 35/28* (2013.01); *A61K 35/39* (2013.01); *G01N 33/5044* (2013.01); *G01N 33/54393* (2013.01); *G01N 33/74* (2013.01); *C12N 2502/1358* (2013.01); *C12N 2533/12* (2013.01); *C12N 2535/00* (2013.01); *G01N 2333/62* (2013.01)

(58) Field of Classification Search
CPC ................ C12N 5/0676–5/0678; A61K 35/39
See application file for complete search history.

(56) References Cited

U.S. PATENT DOCUMENTS

| | | | | |
|---|---|---|---|---|
| 2003/0109036 A1* | 6/2003 | Wu | ...................... | C12N 5/0676 435/366 |
| 2003/0129173 A1* | 7/2003 | Al-Abdullah | ........ | C12N 5/0676 424/93.21 |
| 2008/0103606 A1 | 5/2008 | Berkland et al. | | |
| 2010/0233239 A1 | 9/2010 | Berkland et al. | | |
| 2011/0177132 A1* | 7/2011 | Allon | ................... | C12N 5/0655 424/93.7 |

FOREIGN PATENT DOCUMENTS

| | | |
|---|---|---|
| EP | 2221362 A1 | 8/2010 |
| RU | 100516 U1 | 12/2010 |
| WO | 2010/094747 A1 | 8/2010 |
| WO | 2011/126921 A2 | 10/2011 |
| WO | 2012/123712 A1 | 9/2012 |

OTHER PUBLICATIONS

Bhaiji et al, Journal of Biomedical Material Research Part A, Mar. 2012, vol. 100A, pp. 1628-1636.*
Rasmusson et al, Upsala Journal of Medical Sciences, Mar. 2011, vol. 116, pp. 8-17.*
International Search Report and Written Opinion from co-pending PCT/US2013/064583 mailed Jan. 30, 2014 (8 pages).
Gormony. Kletki Langergansa., [Online] 2009, page L-4 Retrieved from the Internet: <URL:http://hormone.com.ua/hormonipodgelud-gelezi-kletki- langergansa.html> [retrieved on Jan. 17, 2014] (3 pages)—with translation (4 pages) (7 pages total).
Kletochnaya terapiya pri sakharnom diabete. Tsentr Mediko-Biologicheskikh Tekhnology, [Online] Feb. 8, 2006, page L-5 Retrieved from the Internet: <URL:http://www.cmbt.su/eng/science/science78.html> [retrieved on Jan. 17, 2014] (5 pages) with translation (6 pages) (11 pages total).
'Proryv v transplantologii: inektsiya stvolovykh kletok pozvolila izbezhat ottorzheniya.' Medicusamicus, [Online] May 17, 2011, page L Retrieved from the Internet: <URL:http://crimea-med.net/index.php?/topic /1426-proriv-v-transplantologii> [retrieved on Jan. 17, 2014] (1 page) and translation (2 pages) (3 pages total).
'Uchenye razgadali sakret lechebnogo effekta kurkumy, Tekhnologii' Novosti- Aserbaidzhana, [Online] Apr. 20, 2009, page L Retrieved from the Internet: <URL:http://novosti.az/tech/20090420/42824637-print.html> [retrieved on Jan. 17, 2014] (1 page) with translation (2 pages) (3 pages total).
Ramachandran, Karthik, A Platform Technology for Optimized Production of Islet-like Spheroids and Other 3D Cell Spheroids for Applications in Drug Discovery and Regenerative Medicine, Apr. 10, 2012, Submitted to the Bioengineering program and the Graduate Faculty of the University of Kansas in partial fulfillment of the requirements for the degree of Doctor of Philosophy (131 pages).
Supplementary European Search Report in Corresponding European Application No. EP 13846713.9 issued Apr. 22, 2016 (8 pages).

* cited by examiner

*Primary Examiner* — Allison Fox
(74) *Attorney, Agent, or Firm* — Hovey Williams LLP

(57) ABSTRACT

Described herein are 3-dimensional clusters of reaggregated cells comprising cells reaggregated from at least two different cell sources, such as different cell types, different donors, and combinations thereof. Methods of making, using, and cryopreserving these 3-dimensional clusters of reaggregated cells are also described herein.

8 Claims, 14 Drawing Sheets

(A)

(B)

Cryopreservation of single cells

Upon thawing, cells are loaded in MicroMold

Muti-donor 3D spheroids are produced

000
ASSAYS USING A MULTI-DIVOT PLATFORM AND MULTI-SOURCE, MULTI-CELL TYPE CLUSTERS

CROSS-REFERENCE TO RELATED APPLICATIONS

The present application is the U.S. National Stage of PCT/US2013/064583, filed Oct. 11, 2013, which claims the priority benefit of U.S. Provisional Patent Application Ser. No. 61/715,570, filed Oct. 18, 2012, entitled IMPROVED RELIABILITY OF ASSAYS USING A MULTI-DIVOT PLATFORM AND MULTI-SOURCE, MULTI-CELL TYPE CLUSTERS, each of which is incorporated by reference in its entirety herein.

BACKGROUND OF THE INVENTION

Field of the Invention

The present invention relates to multi-source, multi-cell clusters and methods of making, using, and cryopreserving the same.

Description of Related Art

Three-dimensional ("3-D") cell clusters exhibit properties not seen in conventional two-dimensional cell culture. Islets of Langerhans are cell clusters within the pancreas composed of a variety of cell types including alpha-, beta-, and delta-cells, and are responsible for the maintenance of blood glucose level. Lymphocyte destruction of beta-cells (insulin-producing cells) or failure to utilize insulin are the hallmark events that result in type 1 and type 2 diabetes, respectively. Isolating islets from the pancreas of donors provides tissue that can be used for research, transplantation and drug discovery in order to develop therapies for diabetes. Once isolated from their natural location within the pancreas, islets exhibit diminished survival and function, both in vitro studies and soon after transplantation. Within the pancreas, islets are immersed with their native blood supply. After isolation, diffusion becomes the primary means of oxygen, glucose, and nutrient transport into the core of isolated native islets. Empirical modeling of diffusion barriers in native, isolated islets has demonstrated that only the outermost layers of cells are exposed to glucose and sufficient oxygen levels, resulting in core cell death. Engineering optimal islets provides a means to overcome the diffusion barriers affected by islet size limitations.

While 3-D cell clusters, such as islets, can be engineered using a variety of techniques, they still have many problems when used in different applications. For example:

Non-uniform cell number and composition in each cluster
High diffusion barrier
Not compatible with the pharmaceutical industry high-throughput instruments
Not scalable to high-throughput needs
Not able to maintain long-term experiments Improvements in micro-mold technology (US 2010/0233239; US 2013/0029875, both incorporated by reference herein in their entireties) allow the creation of high numbers of 3-D cell clusters, such as islets reaggregated from individual islets cells in the micro-mold. However, even with these advances, limitations still exist including inconsistent response between donors to test compounds, and the fact that 3-D clusters cannot be stored and shipped without significant loss of tissue. Described herein are new methods and devices that overcome these and other problems, resulting in new applications of 3-D cell clusters.

SUMMARY OF THE INVENTION

The present invention is broadly concerned with 3-dimensional clusters of reaggregated cells comprising cells reaggregated from at least two different cell sources, such as different cell types, different donors, and combinations thereof.

Methods of forming 3-dimensional clusters of reaggregated cells are also described herein. The methods generally comprise providing a micro-mold as described in US 2010/0233239 or US 2013/0029875, incorporated by reference herein, and single cells from at least two different sources. All references to "MicroMold," "micromold," "micro-mold," or "micro mold" refer to the same general micro-molds, as described in US 2010/0233239; US 2013/0029875, and described herein. In general, the micro-molds comprise a non-adherent, divoted substrate comprising a substantially planar top surface, wherein the substantially planar top surface comprises a plurality of divots formed therein. The single cells are introduced into the divots, wherein each divot contains a mixture of single cells from at least two different sources. For example, the single cells are dispersed from the selected tissue and then loaded, plated, or seeded onto the micro-mold wherein they settle into the recesses of the divots. The micro-mold is incubated under cell culture conditions, wherein the single cells in each divot reaggregate into a 3-dimensional cell cluster comprising cells reaggregated from at least two different cell sources.

Methods of building immunotolerance in a transplant recipient are also described herein. The methods generally comprise providing stem cells from a donor, and injecting the donor stem cells into the recipient. A 3-dimensional cluster of reaggregated cells as described herein comprising stem cells from the donor and tissue cells to be transplanted is then transplanted (e.g., injected) into the recipient. Advantageously, the recipient requires lower amounts of immuno-suppressing agents, if any, after this procedure.

Additional methods of building immunotolerance in a transplant recipient are also described herein. The methods generally comprise providing a 3-dimensional cluster of reaggregated cells from at least two different cell sources, wherein at least one cell source comprises stem cells from the recipient and at least one cell source comprises donor tissue to be transplanted. The 3-dimensional cluster of reaggregated cells is transplanted into the recipient. Advantageously, the recipient requires lower amounts of immuno-suppressing agents, if any, after this procedure.

Also described herein are methods of screening xenobiotic test compounds. The methods generally comprise providing a multi-source, 3-dimensional cluster of reaggregated cells as described herein. The 3-dimensional cluster is exposed to a xenobiotic test compound, and the response of the 3-dimensional cluster to the xenobiotic test compound is analyzed. Advantageously, the 3-dimensional cluster provides an averaged response in one step as opposed to analyzing each cell source individually and calculating an averaged response.

Methods of cryopreserving 3-dimensional cell clusters are also described herein. The methods generally comprise suspending a 3-dimensional cluster in freezing media, and cryopreserving the 3-dimensional cluster under controlled rate freezing at a rate of $-1°$ C./min to yield a cryopreserved 3-dimensional cell cluster. The freezing media comprises cell culture media, curcumin, and a cryoprotectant. In one or more embodiments, the 3-dimensional cluster of reaggregated cells is an engineered islet. Advantageously, due to the improved diffusion barriers of the engineered islets, these islets have increased viability as compared to a native cryopreserved and thawed islets.

Also described herein are methods of cryopreserving cells for 3-dimensional cell clusters. The methods generally comprise dispersing cells from a tissue (e.g., pancreatic tissue) into single cells, and suspending those single cells in freezing media. The freezing media comprises cell culture media, curcumin, and a cryoprotectant. The single cells are then cryopreserved under controlled rate freezing at a rate of −1° C./min to yield cryopreserved single cells. The cryopreserved single cells are then thawed and transferred to a micro-mold, each containing a plurality of the thawed single cells; and incubated under cell culture conditions, wherein the single cells in each divot reaggregate into a 3-dimensional cell cluster comprising cells reaggregated from the cryopreserved and thawed single cells. Advantageously, for example, when the inventive method is used to create engineered islets, these islets have increased viability as compared to native cryopreserved and thawed islets.

DETAILED DESCRIPTION

The present invention is concerned with improved 3-D cell clusters and methods of making, using, and storing the same. Embodiments of the invention are particularly useful in forming reaggregated clusters of cells that approximate native 3-dimensional tissues, such as islets, tumors, and the like.

As used herein, the term "islet" refers to a group of specialized cells in the pancreas that make and secrete hormones. An islet generally contains one or more of the following cell types: (1) alpha cells that make glucagon, which raises the level of glucose (sugar) in the blood; (2) beta cells that make insulin; (3) delta cells that make somatostatin which inhibits the release of numerous other hormones in the body; (4) pancreatic peptide producing PP cells; (5) D1 cells, which secrete vasoactive intestinal peptide; and (6) EC cells which secrete secretin, motilin, and substance P. As used herein, the term "islet cell" refers to any individual cell found in an islet. The islet cells used in embodiments of the present invention are preferably a combination of insulin-producing beta cells with other islet cell types. As used herein, the term "native islet" refers to intact islets isolated from a mammalian pancreas. Other types of primary cells are also contemplated for use herein, wherein the term "primary cell" refers to cells isolated directly from living tissue, as contrasted with established cell lines.

As used herein, the term "reaggregated islet" is used synonymously with "engineered islet" and refers to a 3-D cluster of islet cells formed in vitro through self-directed assembly. These reaggregated islets are also referred to as Kanslets™. Preferably, the reaggregation of individual islet cells into engineered islets is influenced by the physical dimensions of the divots in the micro-mold. Likewise, references to "reaggregated" cell clusters refer to 3-D clusters of cells formed in vitro through self-directed assembly. The term "spheroid" is also used herein due to the generally spherical shape of the clusters. Reaggregating tissue in an optimized manner using the engineered micro-mold approach has immense impact for three-dimensional tissue production and its subsequent use in research, drug discovery, and the clinic.

Figure 1:
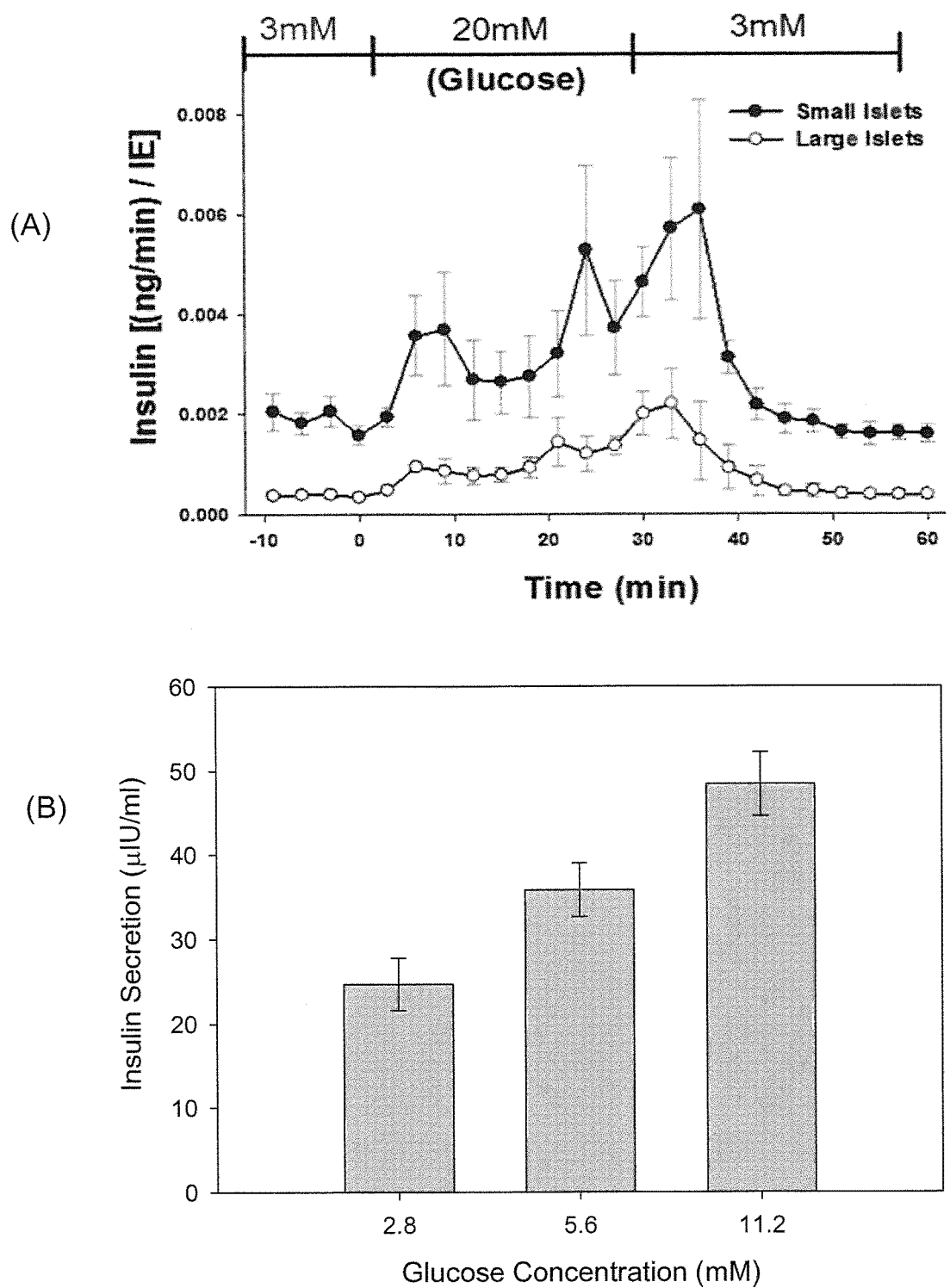
FIG. 1(A) is a graph comparing the glucose-stimulated insulin release from large and small islets from the same donor; (B) shows the response to increasing doses of glucose in Kanslets derived from a mixture of large and small islets from the same donor.

When conducting studies on the effect of specific drug compounds on animal or human tissue, the variability between donors interferes with the interpretation of the results. Even with information about the health of a donor, the purity, and viability of the tissue, the results obtained vary greatly from donor-to-donor. This high variability results in inconsistent responses to test compounds and other assays. Even more frustrating is the variability that occurs within cells and tissues from the same donor. For example, it has been reported that small islets release more insulin in response to high glucose concentrations than large islets (MacGregor et al., 2006). FIG. 1(A) illustrates this point. Islets taken from the same donor were separated into large and small sizes and exposed to high glucose at time 0. The small islets had a significantly higher release of insulin at normal and high glucose (20 mM) concentrations compared to the large islets. Thus, even islets from the same donor demonstrate variations in their response to standard stimulants. However, this variability can be reduced when the islets from a single individual are dispersed into single cells and reaggregated into Kanslets that contain a mixture of both large and small islets, as shown in FIG. 1B. This reduced variability can be identified by the smaller standard error bars. In addition, the standard deviation is greater than 2 times smaller in the mixed Kanslets than combining the response of large and small islets.

Figure 2:
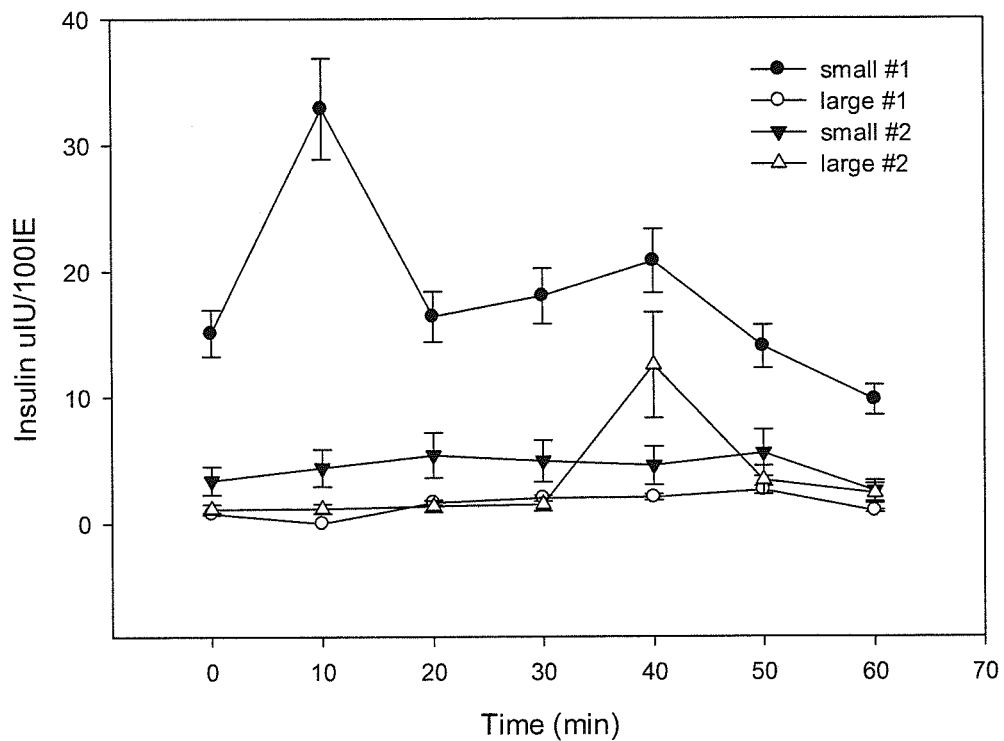
FIG. 2 is a graph comparing the glucose-stimulated insulin release from two different donors with completely different responses. Islets were exposed to high glucose for 60 min, starting at time 0. When the cells were first combined in the micro-mold to make multi-donor clusters, the response to the same concentrations of glucose fell in between the original tissue clusters.
Figure 3:
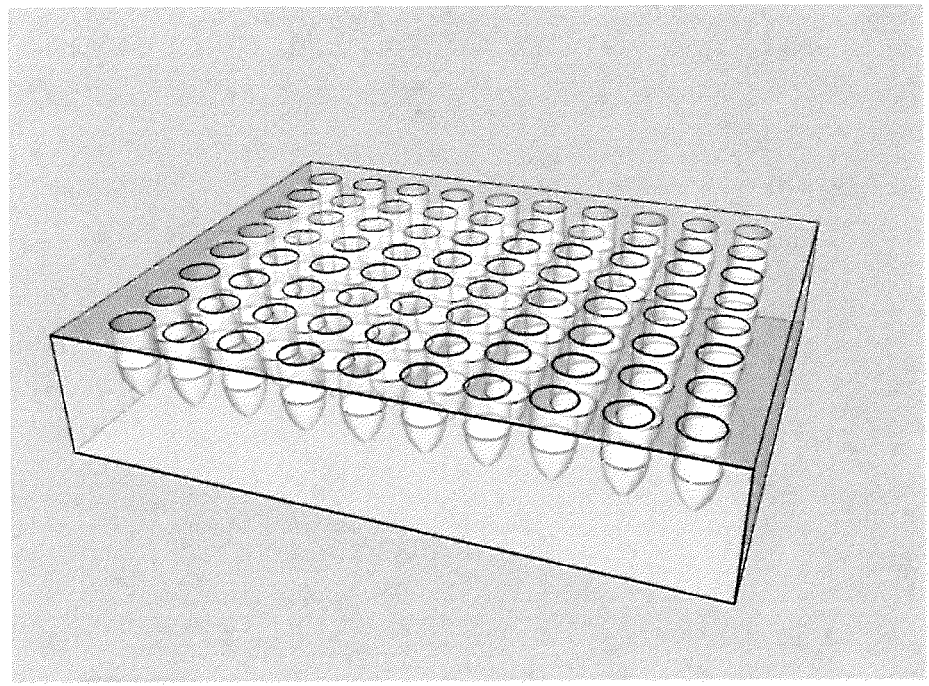
FIG. 3 is a perspective illustration of the design of micro-mold 1.0.
Figure 4:
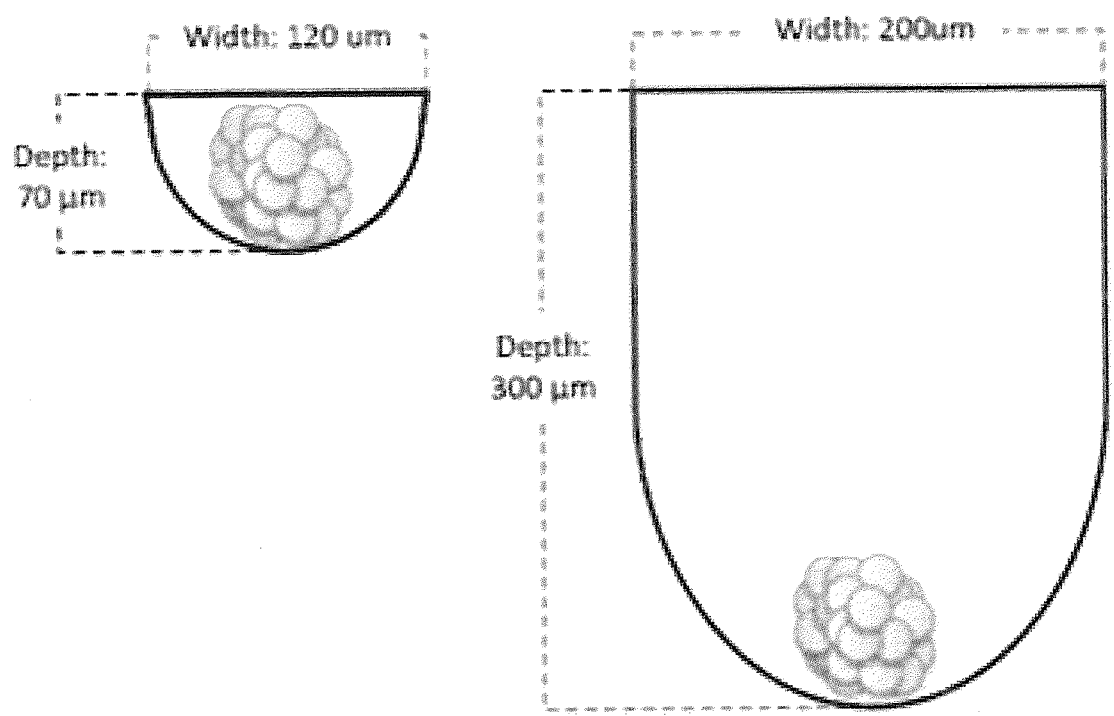
FIG. 4 illustrates that variations in divot depth create more specificity for the end-user.
Figure 5:
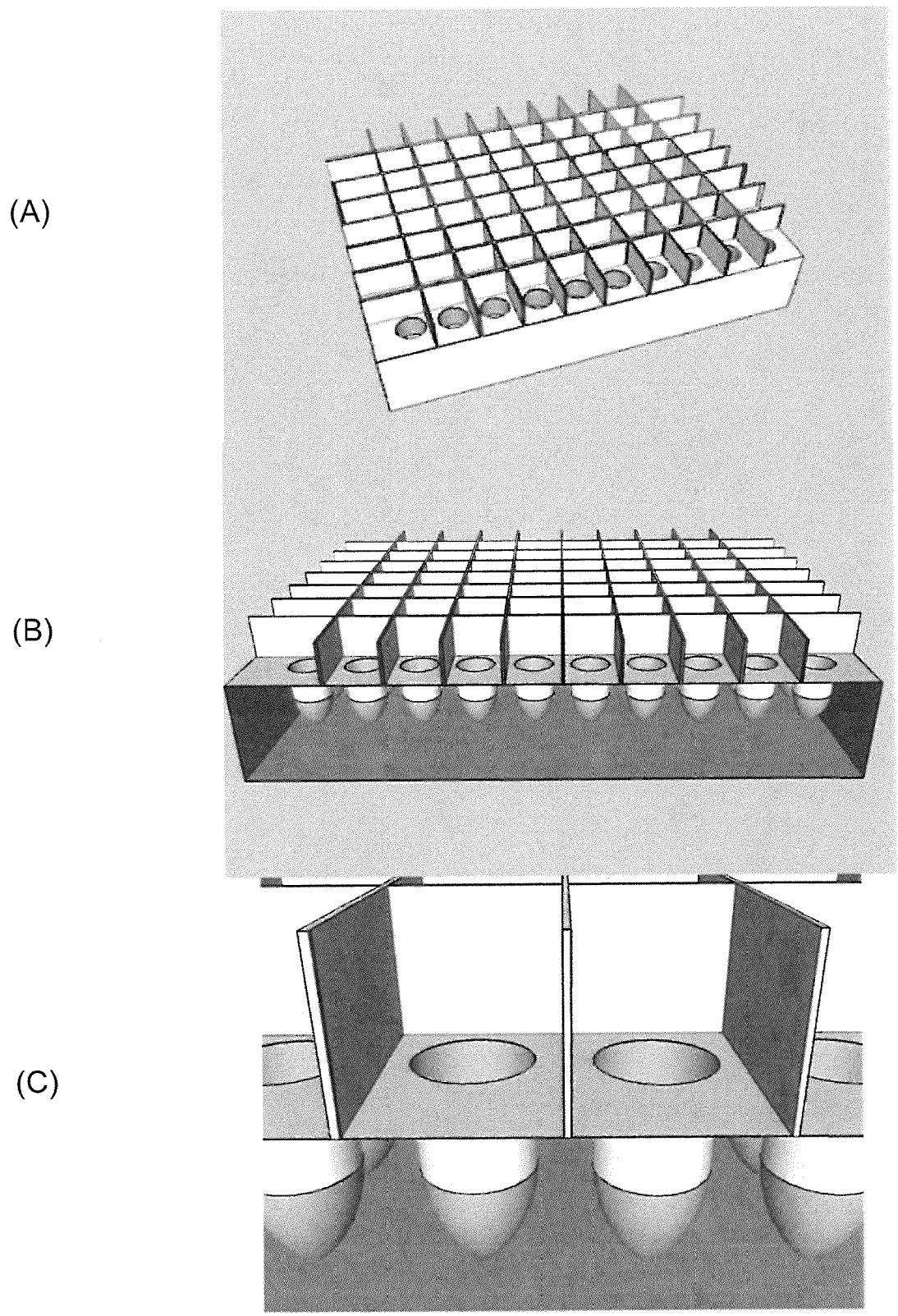
FIG. 5 illustrates the design of micro-mold 2.0 with a single divot/well: (A) perspective view; (B) side view; (C) close-up view.
Figure 6:
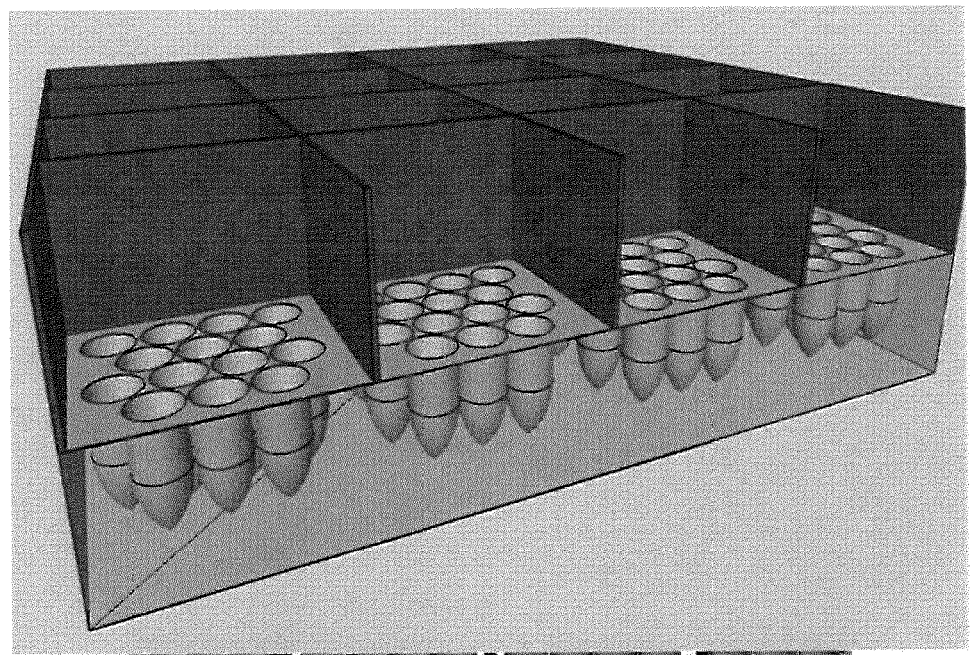
FIG. 6 illustrates the design of micro-mold 2.2 with multiple divots per well: (A) perspective view; (B) top-down view.
Figure 6:
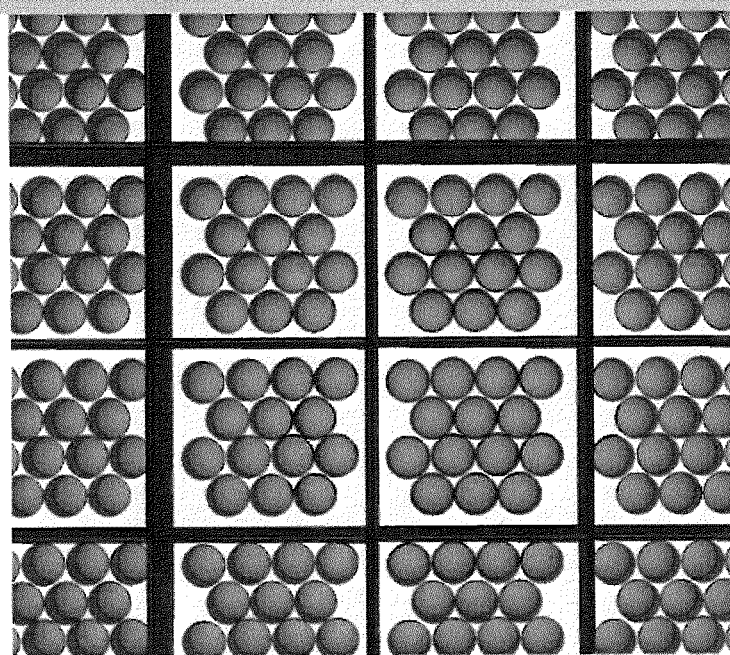
Figure 7:
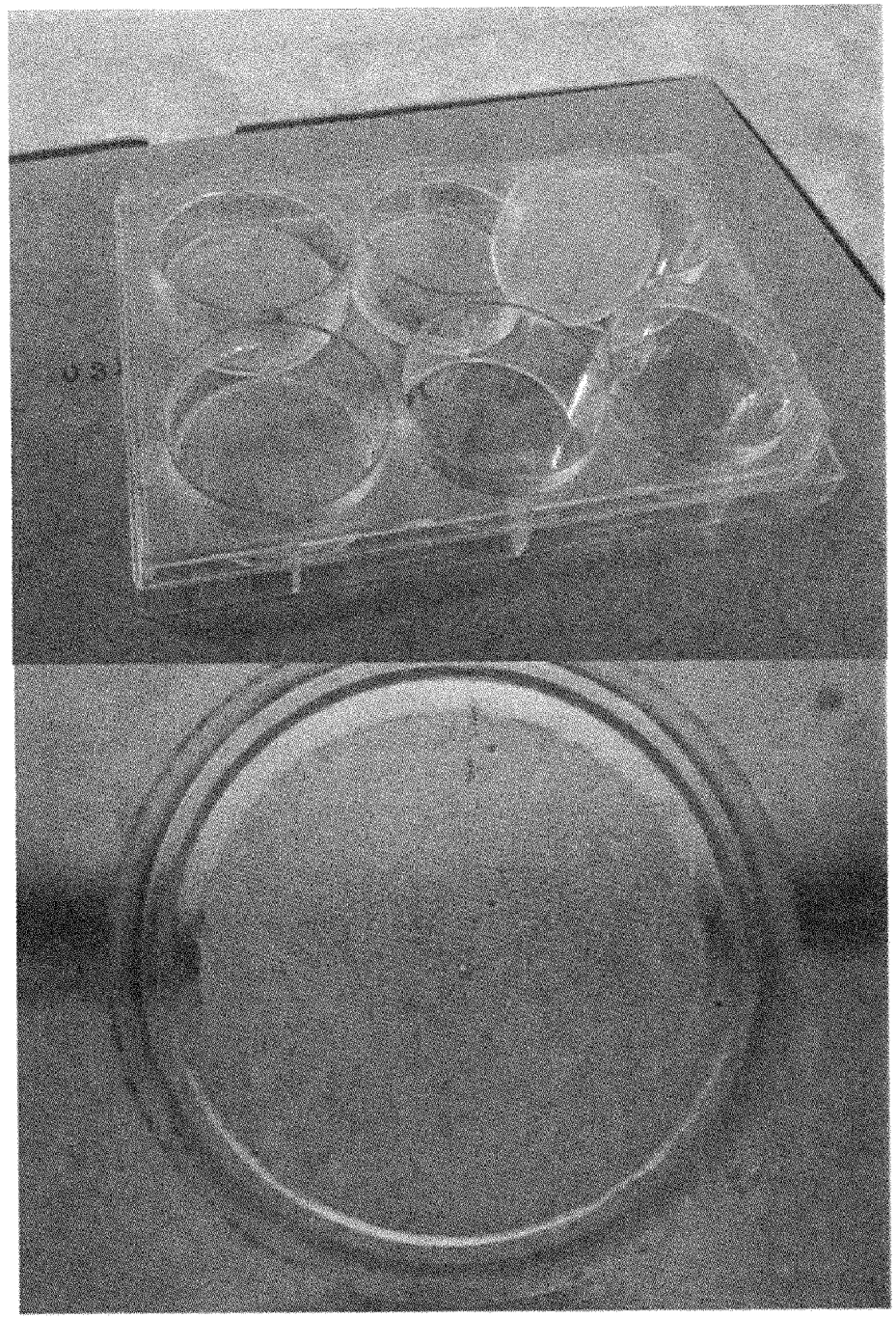
FIG. 7 illustrates that the micro-molds can be designed to fit within the well of other standard plates (A) or can be a free-standing mold (B).

This variability is increased exponentially, when dealing with islets from more than one donor. A stark example of this variability can be illustrated in islets obtained from a set of two human donors. In both cases, the islets used were obtained through the same donor consortium. Both sets of islets were of high purity, high viability, and came from donors that fit the criteria as a suitable drug testing candidate including, but not limited to, being non-diabetic. FIG. 2 illustrates the glucose response of large and small islets from two different human donors. These two donors were well matched: neither was diabetic and both had a body mass index (BMI) that indicated they were in the normal weight category. Donor 1 showed a typical response to high glucose with an increase in insulin secretion from small islets, and no response in large islets. In contrast, donor 2 showed a different result with no insulin secretion from small islets, but a delayed response in large islets (FIG. 2). This simple example shows one of the major complications of using human tissue for drug screening or diagnostic assays that hampers the entire pharmaceutical industry and the biomedical field.

The response variability of islets hampers the discovery of new diabetes drugs, but the same is true for drug discovery for other diseases including (but not limited to): cancer, heart disease, vascular disease, and other endocrine disorders. The inherent variability from person-to-person could be accounted for mathematically by calculating average responses from many donors. However, this process can become time consuming and costly due to the high number of trials necessary to determine significant results for each test compound. When a single screen might consist of 100,000 compounds, the barrier to using human tissue becomes apparent. The donor-to-donor variability and the natural variability to stimulants of cells from the same donor makes it difficult, if not impossible, to use human tissues to screen large numbers of compounds as potential new drugs for diabetes or other pancreatic endocrine disorders.

Donor-to-donor variability poses difficulties when searching for new therapeutics or conducting research, whether the tissue donor is human or other species. As noted above, it is possible to solve this problem by conducting a large number of runs of a single experiment to produce significant results. This can be coupled with complex statistical analysis aimed at finding the true "average" response. These studies are costly and lengthy, and this complication increases exponentially in a high-throughput settings. Our technology proposes the use of multi-donor 3-D spheroids, formed by mixing cells from a variety of donors together to produce 3-D cell clusters that represent a more "averaged" response. The micro-mold production and the reaggregation of cells into 3-D clusters using the molds has been described in US 2010/0233239 or US 2013/0029875 (see also FIGS. 3-7). Embodiments of the present invention are concerned with new solutions for drug testing using 3-D cell spheroids, which can be organotypic or form a completely new (non-naturally-occurring) cell cluster. These multi-source cell clusters provide a more "averaged" or representative response to xenobiotic test compounds. In some aspects, the invention uses newly designed micro-molds that allow more clusters per drug testing well. These new multi-source cell clusters can also be produced using any technology that enhances spheroid production including, but not limited to, the hanging drop method, rotation or gravity assisted methods, or other suitable techniques.

While most other techniques to develop 3-D cell clusters solely rely on cultured cell lines, the micro-mold technology allows the creation of multiple sources of starting material including (but not limited to) cell culture lines, fresh human tissue, cryopreserved human tissue, fresh animal tissue, cryopreserved animal tissue, and genetically engineered cells from any source. In one aspect, the 3-D cell clusters can comprise cells from different sources. A "source," as used herein, refers to obtaining cells or tissues from various donors, biopsies, tissue resections from different tissue samples or different tissue sources, different animals harboring cells (species or strains), or primary, secondary, immortalized, or transformed/engineered cells. The cells may be derived (directly or indirectly) from any suitable human or animal donor, including human, porcine, simian, canine, feline, bovine, equine, ovine, leporine, or murine sources, among others. Examples of such tissues would include (but not be limited to) organs, chondrocytes, osteocytes, myocytes, vascular cells, skin/epithelial cells, and/or stem cells (embryonic and adult). Cells or tissue that are considered to be obtained from "different" sources include those obtained from donors of different genders, genotypes, ages, races (e.g., Caucasian, etc.), enzymatic or metabolic activities, species, or disease or health states (e.g., tissue from a diabetic donor, tissue from a donor with normal insulin production, tissue from a donor with heart disease, cancerous tissue, etc.). "Different" sources also includes different cell types and functions. For example, multifunctional clusters can also be prepared which secrete more than one hormone (e.g., insulin-producing and thyroid hormone-producing clusters).

1. Multiple Cell Type Clusters

3-D cell clusters could be formed from starting material from a single organ, or could comprise starting material from multiple tissue types. For example, cardiac myocytes could be mixed with vascular endothelial cells to create a 3-D cell cluster comprising myocytes and vascular endothelial cells to be implanted in a diseased heart. The endothelial cells would enhance blood vessel formation to the new heart cells. Likewise, islet clusters could be formed with vascular endothelial cells again with the goal of speeding vessel formation into the transplanted islets. In some cases, multiple cell types can be harvested from a single organ, and would be considered multi-sourced. The multi-cell type clusters could be formed from human tissues or from any animal species, or a mixture of species. For some types of research, 3-D cell clusters can be made with cancer cells.

A. Protocols for Multi-Cell Type Clusters

When creating multi-cell type 3-D cell clusters, two basic protocols can be followed.

1. Whole tissue containing multiple cell types such as hepatocytes, fibroblasts, endothelial cells, and smooth muscle cells could all come from the same liver sample. After dispersion of the tissue, using enzymes or other standard procedures, the single cells would remain in a mixture of cell types and would be dispersed a one aliquot into the micro-mold. Upon loading into the micro-mold and entering the divots, the mixture of cell types bind to each other forming a multi-cell type 3-D cell cluster.

2. Alternatively, a 3-D cell cluster with an enhanced fraction of one cell type may be desired. The starting material can be derived from pure or semi-pure fractions of individual cells types. For example, cells from the pancreas would be separated using flow cytometry into islet beta cells, alpha cells and delta cells. In order to form 3-D clusters that had the same average naturally-occurring ratio of these three cell types, as the native islet, the separated fractions would be mixed in a specific ratio. In the case of islet cells, that ratio could be about 70% beta, about 20% alpha and about 10% delta. The exact ratio of the cell types would be determined by the end user and has unlimited possible iterations. For example, in one or more embodiments, cell ratio in the clusters could be: from about 60-90% beta cells, from about 10-40% alpha cells, and from about 0-10% delta cells, with the proviso that alpha is greater than delta. The mixture of cells would then be loaded into the micro-mold as described previously.

One specific example of protocol #2, includes the combining of organ tissue with stem cells. In one example, individual islet cells could be mixed with undifferentiated cells (i.e., stem cells) prior to loading in the micro-mold. This procedure would result in a hybrid islet/stem cell 3-D cluster. There are multiple purposes for such an approach. In one example the stem cells may differentiate into another cell based on the chemical and physical signals from the differentiated cells in the cluster. Alternatively, the stem cells could be mixed into the hybrid 3-D cell cluster as a way to confer immunotolerance into the recipient of a transplant with said hybrid clusters. We have utilized ratios of islet cells to stem cells of 2:1, 1:1 and 1:2, all with successful resulting engineered islets. All ratios of the starting cell types could be varied by the end-user with endless combinations. For example, other ratios include islet to stem cell ratios of 1:6, 1:3 and up to 100:1. It will be appreciated that the ratio will also depend somewhat on the number of cells used in each cluster. In one or more embodiments, there are at least 7 cells in the hybrid cluster (6 islet cells and 1 stem cell). For example, this cluster could consist (essentially) of 3 beta cells, 2 alpha cells, 1 delta cell, and 1 stem cell. In other embodiments, the reengineered islets will comprise about 50-100 islet cells and appropriate ratios of stem cells. In one or more embodiments, stems cells account for about 10% or even about 25% of the total cells in the 3-D cluster. In this same example, rather than mixing the native cells with stem cells, the hybrid could also be formed with native cells and engineered cells, according to any of the ratios mentioned above.

One important application concerning stem cell/differentiated cell mixtures would be to build immunotolerance in a transplant recipient. In one example stem cells from the donor would first be injected into the recipient to prime the recipient's immune system. Subsequently the hybrid stem cell/differentiated cell cluster would be transplanted into the recipient. If immunotolerance is obtained, the recipient would require no, or lower amounts of, immunosuppressing agents post-transplant. In another embodiment, the recipients own stem cells could be mixed with transplant cells from a donor and reaggregated into a 3-D cluster for transplantation. The recipient's own stem cells can help decrease the chance of rejection of the transplanted cells in the 3-D cluster. This embodiment is described more particularly below with respect to bone marrow stem cells and donor islet cells.

In the case of engineered cells, genetically- or chemically-engineered cells could be mixed with the same cell type or different tissues using native or other genetically-engineered cells. For example, native cancerous multiple myeloma cells generally do not adhere to each other strongly enough to produce 3-D clusters that can be removed from the mold. One could either genetically or chemically alter the cells when in the single cell form, before loading into the mold in order to enhance cell-to-cell binding, and thus formation of the 3-D cluster. Alternatively, the multiple myeloma cells could be mixed with other cells types such as fibroblasts or stem cells, which would enhance cell-to-cell binding. In another embodiment, a 3-D cluster of stem cells could be first formed, and then the multiple myeloma cells (or other cell type) could be mixed with the 3-D cluster, or cells could be added at different time points rather than at the exact same time. This alternative technique would build a multi-layer cluster or cause the cells to merge on their own. It will be appreciated that the cell isolation procedure, cluster formation media, conditions and time can all be optimized to the cell types being used.

One example of multiple cell type clusters is the stem cell/adult cell. Rather than mixing stem cells with differentiated cells to create a hybrid cell cluster, one could also begin with stem cells and differentiate them into a single cell type or multiple cell types. For example human stem cells could be formed into cartilage-producing chondrocytes and bone-forming osteoblasts. The 3-D cell clusters from these different products could then be mixed and placed in a joint to build an improved bony surface and increase cartilage.

Epithelial cell clusters or stem cell clusters could be used as fillers to fill defects, scars, or void spaces.

B. Multi-Donor Cell Clusters

Figure 8:
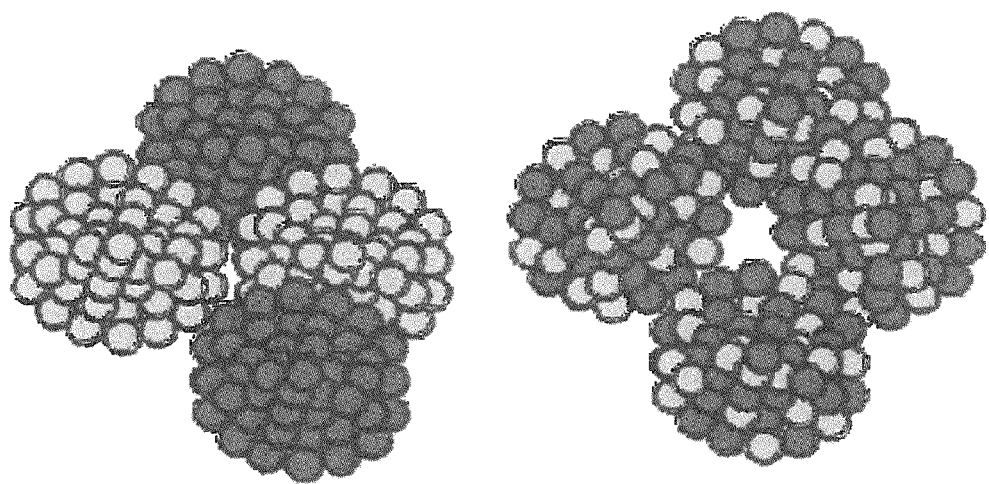
FIG. 8 illustrates engineered islets from two different donors (symbolized by different colors) are mixed (left); and unique engineered islets that contain cells from each of the two donors (right)

In this embodiment, there are two possible pathways to multi-source 3-D cell cluster formation. The first pathway would produce the cell clusters using tissue from a single donor, then after the clusters were produced, they would be combined with the clusters from a number of other donors and used as a mixed experiment (FIG. 8, left). The second pathway entails dispersing cells from a variety of individuals into single cells, mixing the cells together, and then producing individual cell clusters that represent mixed cells from several donors (FIG. 8, right). This would result in individual cell clusters composed of several cell types from several donors. The ratio of cells can preferentially be mixed at a 1:1:1 ratio or any other specified ratio. Cells could be counted before mixing them to ensure appropriate mixtures. For instance, 1 million cells from donor A can be mixed with 1 million cells from donor B. The mixed cell population would then be seeded onto the micro-mold (FIGS. 3-7) or any other suitable mold or scaffold. Seeding could take place by mixing the cells first and seeding once onto the scaffold or mold, or could occur with sequential seeding, as a tissue printing instrument or cell dispensing unit would do. Once the multi-donor clusters are produced, experimentation could occur providing an averaged result in one step as opposed to running each donor individually and then having to statistically determine the commonalities between results. One application of the mixed bone marrow stem cells/islet cluster would be in the field of tissue transplantation. Bone marrow stem cells could be harvested from the recipient of a transplant prior to the transplant itself or from the donor of the transplant. Those stem cells would be mixed with the donor islet cells (or other cells types depending on the pathology to be treated) using the micro-mold. The resulting hybrid spheroid would be a combination of the recipient's own stem cells and the islet cells from another donor.

Unique to this technology is the ability to, not only mix the cells of several donors into a single batch, but to specify traits or criterion for specific experiments. For instance, a multi-donor study could be specifically run on cells from female or male individuals. Other groups could include limiting multi-donor spheroids to a specific race, age, sex, geographical region, body mass index, disease state, or any possible variation of this theme.

When examining sex differences in disease states, female-specific and male-specific cell clusters might be used. This would apply to humans and all other animal species. If the target disease were transmitted from one sex to another, single cell clusters with both sex-based cells could be created so that the cells from a male and female were in direct contact within the cell cluster. Similarly, when examining species differences in disease states, cell clusters of different species might be used. This would apply to humans and all other animal species. For example, when testing drugs or therapeutics with the potential to alter the transmission of agents, such as prions, that can cross species, cell clusters from the different infecting species may be combined. If the target disease were transmitted from one species to another, single cell clusters with both species-based cells (e.g., hybrid clusters) could be created so that the cells from both species were in direct contact within the cell cluster.

C. Species-Specific and Multi-Species Cell Clusters

The examples provided previously, mainly focused on human tissues and the formation of hybrid cell clusters from that starting material. However, the donor tissue may be from non-human sources. In animals, multi-donor cell clusters could be used to make species-specific clusters. For example, to find new drugs to treat common respiratory problems in cattle, bovine lung clusters could be formed for drug screening. The clusters could also be made to be strain-specific. It also allows the screening of large numbers of drugs for a subpopulation. A subpopulation could be a specific ethnic group, a strain of animal, or it could be a subpopulation with a specific disease. For example, it may be difficult to obtain enough biopsy material from a rare solid tumor from one person, but with the procedure described here, biopsy material from many people with the same sub-type of tumor could be mixed. This would provide enough material for a small or rare tumor to be able to screen 1000's of potential drug compounds at one time. Alternatively, people with rare genetic disorders could be grouped and their tissues combined to provide enough non-cultured tissue for screening.

Species-specific donor populations are important in addressing animal health and the human food chain. Specific species and strains of animals require health treatment options that are unique for their subpopulation. For example, Burmese cats contract diabetes at a higher rate than other cat strains. Thus, one would want to study and test islet cell clusters specific to that strain of animal. Multi-donor Burmese cat engineered islets could be useful in testing new drugs to treat the high degree of diabetes in these animals. This can provide a simplified approach to answering questions about drug responses or diagnostic tests within population subgroups. Joint problems, specifically in dogs and horses are a serious and costly problem.

Injection of chondrocytic cell clusters that were species-specific, would have great healing potential. Alternatively, drug screening for species specific problems, such as dog tumors could be done using 3-D cell clusters from the original tumor tissue. This could be used as an in vitro screening mechanism to screen large numbers of experimental compounds before in vivo testing. Alternatively a portion of a biopsied tumor could be dispersed into single cells and possible commercially-available chemotherapy drugs could be tested on the 3-D cell clusters from that dog's specific tumor. The results of the kill rate on the tumor from that dog would guide the veterinarian in his/her choice of therapeutic approach.

There may be times when multi-species 3-D cell clusters are required. For example, when one is studying the transmission of disease from one species to another, having cell clusters from multiple species in the same experimental aliquot would be useful. This would be done following the procedures described above and illustrated in FIG. 8 (left). Alternatively, if close contact between cells is required to transmit the disease, then 3-D cell clusters with multiple species within the same cluster would be needed (FIG. 8, right image).

D. Cell Clusters and Scaffolds

While most of the 3-D cell clusters produced by the micro-molds are scaffold-free, it is possible to produce 3-D cell clusters in the micro-molds using scaffolds.

1. Scaffold/Cell Cluster Formation

Bio-based or cell-produced scaffolds can be created by adding fibroblasts or other cells responsible for producing extracellular matrix to the mold at the time of seeding with the cells of interest. These fibroblasts would produce collagen creating a natural scaffold for the 3-D cell cluster. In addition, growth factors or matrix proteins could be added to the media while the 3-D cell clusters were forming. For example, BD Matrigel™ Matrix (Bedford, Mass.), which contains collagen, laminin, entactin, and growth factors, is a suitable bio-based scaffolding material that could be used in such embodiments. In this example, cells would normally be seeded into the micro-mold. On certain days during the cluster formation process hormones or other proteins or scaffold-enhancing products would be added to the media to enhance cluster formation and scaffold development. One example would be the mixture of cardiac myocytes with fibroblasts and vascular endothelial cells and extra media amino acids. This iteration would increase vessel formation, along with scaffolds that would penetrate the cardiac cluster to increase the penetration of the vessel into the core of the cluster where blood vessel exchange is critical. Another example comprises adding all the cells together on day one with a media component to initiate cell cluster formation, but then exclude those components from fresh media added on future dates, where that initial addition of components was sufficient for cluster formation. This could also help speed up cluster formation by assistance.

2. Scaffold Addition to Micro-mold

Alternatively, multi-source spheroids could be created within or attached to a scaffold material. For example, when the cell clusters were nearly formed (i.e., day 4 in the micro-mold), scaffold material could be added to the micro-molds and overlaid on the cell clusters. Suction would draw the cell clusters to the scaffold, where they would stick on the bottom surface. This scaffold could be formed of a biodegradable biomaterial. Some suitable biodegradable biomaterials include poly(DL-lactide-co-glycolide) (PLO), polylactic acid (PLA), or poly(lactic-co-glycolic acid) (PLGA). The scaffold could be coated or impregnated with a number of molecules to enhance cell adhesion, cell viability, cell function or alter the immune response to the scaffold material. Alternatively, the size of the pore within a biopolymer may be suitable for natural formation of uniform cells spheroids.

E. Cryopreservation and the Production of 3-D Cell Clusters Using Cryopreserved Tissue A key hurdle to the production of multi-source 3-D spheroids is the availability of tissue sources. Multi-donor human islets are generally only possible when multiple tissue donations are available within days of each other, and thus can be mixed when producing the multi-donor islets (FIG. 8). In order to scale-up the multi-donor product, cryopreservation (or quick deep freezing) presents itself as an ideal solution to storing tissue from donors until enough donors are collected for a particular experiment, transplant or other need.

Unfortunately, researchers face major obstacles when cryopreserving 3-D cell clusters (Lakey et al., 2003). At the core of the issues is cell destruction during the freezing process, leading to decreased viability. As used herein, the term "cell viability" refers to a measure of the amount of cells that are living or dead, based on a total cell sample. High cell viability, as defined herein, refers to a cell population in which greater than 85% of all cells are viable, preferably greater than 90-95%, and more preferably a population characterized by high cell viability contains more than 99% viable cells.

Figure 10:
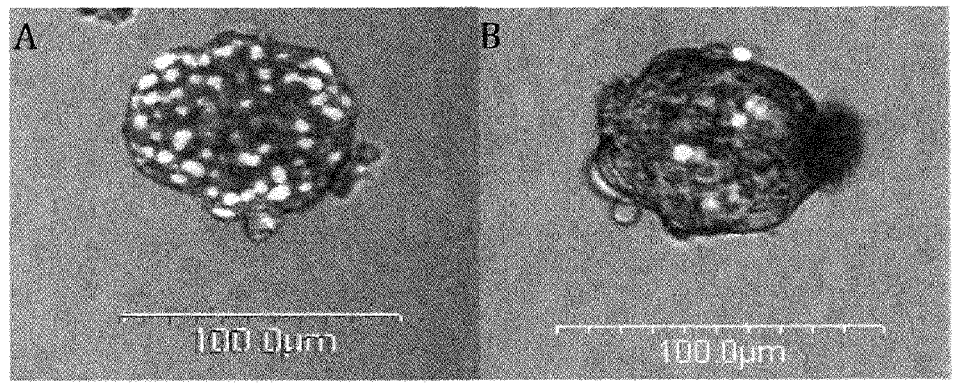
FIG. 10 shows VYBRANT® viability staining of cryopreserved native human islets (A) verses engineered islets produced from cryopreserved, single, dispersed human islet cells (B). The yellow and green stains represent dead cells.

FIG. 10A illustrates the dramatic cell loss that occurs when intact, native islets are subjected to current cryopreservation techniques. Upon thawing, a majority of the cell have died (green and yellow staining of FIG. 10A). This is not only true in our laboratory, but has been published by other labs (Taylor and Baicu, 2009). One explanation for the poor viability after freezing is the diffusion barrier that 3-D tissues inherently possess. Thus, most standard cell cryopreservation protocols work poorly with 3-D cell clusters.

The inventive 3-D clusters of reaggregated cells can be cryopreserved intact and with increased viability over native cryopreserved and thawed islets. The self-directed assembly of the clusters, in which the cells communicate through cell signaling to arrange in the structure according to their respective cellular requirements, increases the overall chances of success for each cell in the structure. In addition, as described in previous work, US 2010/0233239 or US 2013/0029875, the reaggregated clusters have substantially improved (lower) diffusion barriers allowing all cells in the structure substantially equal access to nutrients and cell culture conditions. As demonstrated by the inventive work herein, the 3-D cell clusters not only have improved viability generally, but through modified cryopreservation techniques also have improved viability during cryopreservation, storage, and thawing of intact 3-D clusters. That is, the inventive 3-D cell clusters can be cryopreserved under controlled rate freezing, as described in the working examples, to yield a cryopreserved 3-D cell cluster. These 3-D cell clusters can be stored under liquid nitrogen, and then thawed according to the protocols described herein. Advantageously, due to the improved diffusion barriers of the engineered islets, these islets have increased viability as compared to native cryopreserved and thawed 3-D tissues, such as islets. This is because the cells in the 3-D clusters have substantially equal access to the cryoprotectant and thawing media, and undergo a more uniform freezing and thawing process throughout the entirety of the 3-D structure of the reaggregated cells. This substantially improves viability outcomes.

Figure 11:
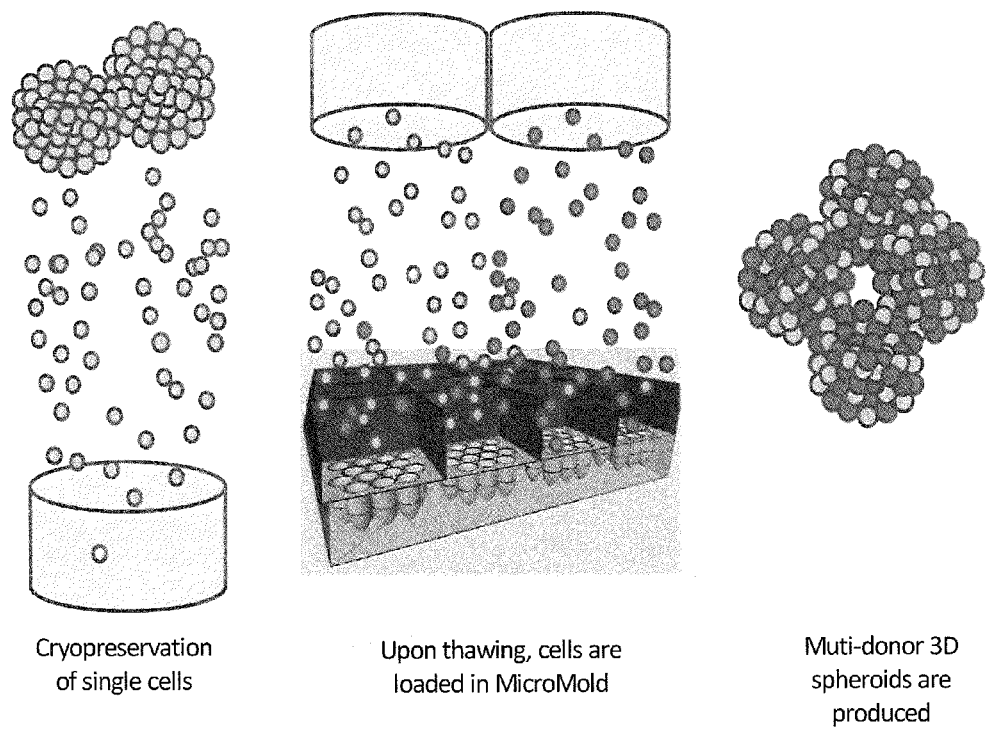
FIG. 11 is a schematic of a cryopreservation procedure. First, native islets are dispersed into single cells for freezing. Upon thawing, the cells are immediately loaded into the micro-mold. The resulting 3-D cell cluster has a higher viability and can be comprised of cells from a single donor or multiple donors.

While cryopreservation of engineered tissues and other small 3-D cell clusters offers an improvement over standard tissue cryopreservation techniques, we can further improve the process with our micro-mold technology. Cryopreserving the single dispersed cells from any tissue results in improved outcomes compared to freezing larger sections of tissue. Thus, in a second protocol for creating and preserving engineered islets, the tissue is dispersed into single cells, which are cryopreserve, and upon thawing, loaded into our micro-molds for 3-D formation as shown schematically in FIG. 11.

In traditional cryopreservation, cells may adhere to the surface of a culture flask or plate and then non-viable cells are washed away 24-48 hours later. Cell cultures are proliferated and expanded to increase the amount of available cells. In the present invention, we have shown that engineered islets can be produced with viability over 99%. With an appropriate cryopreservation protocol to freeze single islet cells, we are able to produce high viability tissues, especially after cryopreservation of the single cell components. Furthermore, we have shown that native islets that do survive cryopreservation have a very short life span, with nearly 100% cell death 72 hours after thawing. Engineered tissues, in contrast, are able to be maintained after thawing for several days without noticeable drops in viability.

This method could also be used for collecting tissue matches for regenerative medicine such as cell clusters for transplantations. For instance, if ideal donor tissue is made available, but no suitable match can be found, the tissue could be saved back as single cells for future engineering and use for an islet transplantation for a diabetic patient later.

This method also allows for drug screening on human islets to be completed in a more efficient manner.

Additional advantages of the various embodiments of the invention will be apparent to those skilled in the art upon review of the disclosure herein and the working examples below. It will be appreciated that the various embodiments described herein are not necessarily mutually exclusive unless otherwise indicated herein. For example, a feature described or depicted in one embodiment may also be included in other embodiments, but is not necessarily included. Thus, the present invention encompasses a variety of combinations and/or integrations of the specific embodiments described herein.

As used herein, the phrase "and/or," when used in a list of two or more items, means that any one of the listed items can be employed by itself or any combination of two or more of the listed items can be employed. For example, if a composition is described as containing or excluding components A, B, and/or C, the composition can contain or exclude A alone; B alone; C alone; A and B in combination; A and C in combination; B and C in combination; or A, B, and C in combination.

The present description also uses numerical ranges to quantify certain parameters relating to various embodiments of the invention. It should be understood that when numerical ranges are provided, such ranges are to be construed as providing literal support for claim limitations that only recite the lower value of the range as well as claim limitations that only recite the upper value of the range. For example, a disclosed numerical range of about 10 to about 100 provides literal support for a claim reciting "greater than about 10" (with no upper bounds) and a claim reciting "less than about 100" (with no lower bounds).

REFERENCES

Lakey J R, Burridge P W, Shapiro A M. Technical aspects of islet preparation and transplantation. Transpl Int. 2003 September; 16(9):613-32.

MacGregor R R, Williams S J, Tong P Y, Kover K, Moore W V, Stehno-Bittel L. Small rat islets are superior to large islets in in vitro function and in transplantation outcomes. Am. J. Physiol. Endocrinol. Metab. 2006; 290(5); E771-779.

Ramachandran et al. Engineering islets for improved performance by optimized reaggregation in a micro-mold. Tissue Engineering. 2013; March; 19(5-6):604-12.

Taylor M J, Baicu S. Review of vitreous islet cryopreservation. Organogenesis. 2009; 5(3):155-166.

EXAMPLES

The following examples set forth methods in accordance with the invention. It is to be understood, however, that these examples are provided by way of illustration and nothing therein should be taken as a limitation upon the overall scope of the invention.

Example 1

Hybrid Stem Cell/Adult Cell Clusters

Figure 12:
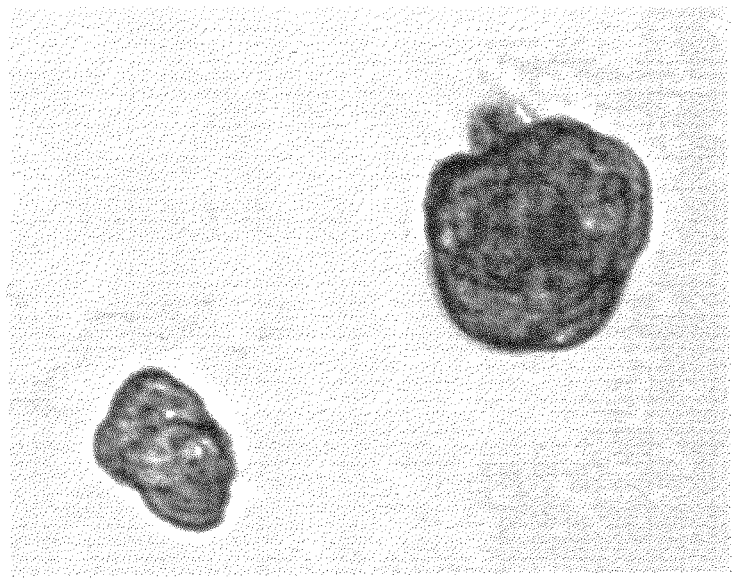
FIG. 12 is an image of a mixture of rat bone marrow stem cells and islet cells producing hybrid cell clusters.

We have been able to create mixed spheroids using adult rat islet cells and rat bone marrow mesenchymal stem cells (FIG. 12). The protocol is provided below. Bone marrow mesenchymal stem cells (BMSCs) were trypsinized from the cell culture flask in which they were cultured and expanded. We have also tested MSC from umbilical cord. The BMSCs were then placed in a tube and the cell number was counted using a hemocytometer. Native/primary pancreatic islets were isolated and broken down into single cells. Briefly, rats were anesthetized by intraperitoneal injection of a mixture of ketamine and xylazine. After the peritoneal cavity was exposed, the pancreatic main duct to the duodenum was clamped, cannulated in situ via the common bile duct, and distended with cold collagenase (CLS1, 450 units/ml; Worthington, Lakewood, N.J.). After excision, the pancreas was incubated for 20-30 minutes with gentle tumbling in a 37° C. incubator. The contents of the tube were washed, passed through a 100 μm mesh screen, and sedimented in a refrigerated centrifuge. The pellet was mixed with Histopaque (density=1.1085) and centrifuged. The islets, collected from the gradient, were sedimented and washed over a sterile 40 μm mesh cell strainer. Islets were placed into a modified DMEM/F-12 medium supplemented with 10% fetal bovine serum (FBS), 1% antibiotic/antimycotic and allowed to recover overnight in an incubator at 37° C. and 5% $CO_2$.

The isolated islets were dispersed into single cell suspensions. Islets were washed twice with calcium- and magnesium-free HBSS (cmf-HBSS) before addition of digestion medium consisting of cmf-HBSS supplemented with 4.8 mM HEPES and papain (5 units/ml; Worthington, Lakewood, N.J.). Suspensions were incubated on a rotator at 37° C. for 20 minutes. Islets were dispersed by trituration using a pipette until the cell suspension primarily contained single cells. The cells were then washed to remove residual papain and transferred to a customized DMEM:F12-based, serum-free islet aggregate culture medium. Occasionally, a sample was taken and cell counts and yield were determined using a hemocytometer.

The isolated islets and BMSCs were mixed in the desired ratios. We have produced islet/stem cell clusters in a 1:6 ratio of islet cells to BMSCs, and in 1:1 ratios. However, the variations in the ratios and number of donor sources from which cells are derived is limitless. This ratio can be determined based on the needs of the experiment/product.

The media for production of the mixed cell clusters consisted of:
DMEM-F:12 with 10% fetal bovine serum and 1% antibiotics; or
CMRL1066 with 10% fetal bovine serum and 1% antibiotics The mixed cells were then cultured on the micro-molds, as described in US 2010/0233239; US 2013/0029875, incorporated by reference herein. Glass micro-molds were fabricated through a multistep process that included thin-film deposition, photolithography, and wet etching techniques. Briefly, pre-cut discs from Precision Glass and Optics (Santa Ana, Calif.) were used for the initial substrate. The glass substrates were cleaned using acid and base piranha solutions and dried at 200° C. to ensure the surface was free of moisture. One surface of the glass substrates was sputtered with a layer of chromium (Lesker Thin Film Deposition System). Positive photoresist (AZ1518) was spin-cast onto the chromium surface and pre-baked at 100° C. for 2 minutes. A transparency mask template was created containing the defined geometry and layout of wells to be etched using computer-assisted design (CAD) in AutoCAD software (Autodesk) and high-resolution transparency masks were printed. The photoresist-coated discs were exposed to UV-light through the transparency mask for 4 seconds. The exposed glass was then post exposure baked at 100° C. for 10 minutes and then immersed in developer (AZ 300 MIF Developer) to pattern the photoresist layer. The chromium layer was subsequently etched (CR7S Chromium Etchant) using the photoresist as an etch mask. The glass substrate was then washed with water and dried with nitrogen. To etch the pattern into the surface of the glass, the disc was wet etched by immersion in a buffered oxide etch (BOE) solution containing a 14:20:66 ratio of $HNO_3$ to HF to $H_2O$ respectively. A profilometer (Tencor Alphastep 200) was used periodically to measure the etched surface and adjustments were made accordingly. The remaining photoresist and chromium layers were removed to reveal the etched micro-mold comprising a plurality of divots formed in the surface of the micro-mold substrate.

Figure 13:
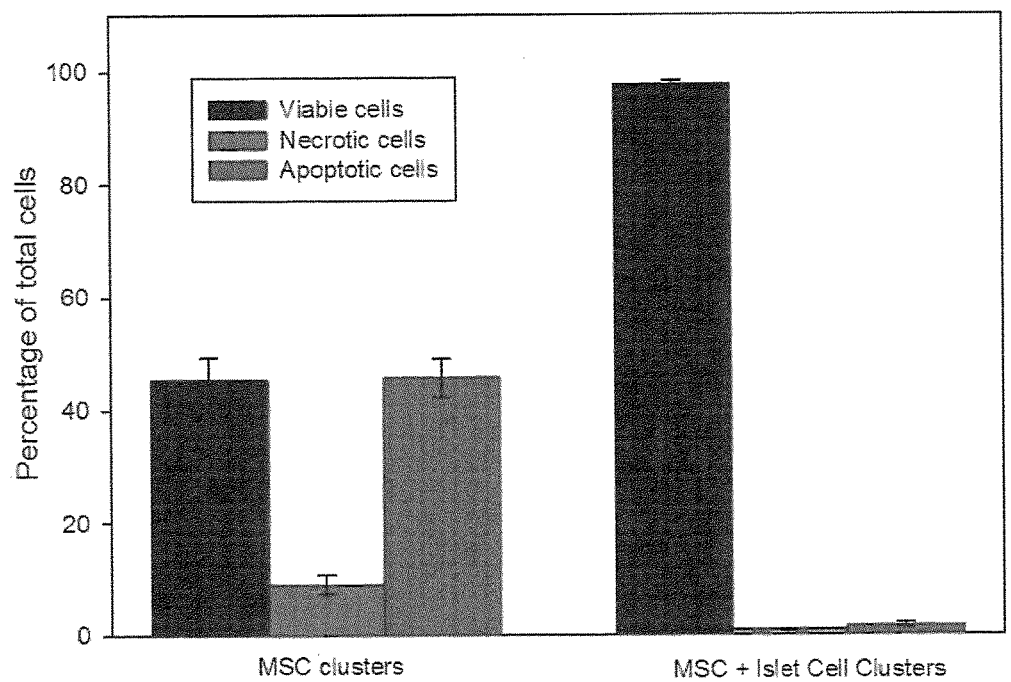
FIG. 13 is a graph showing the viability of cell clusters is improved when the mesenchymal stem cells (MSCs) are combined with islet cells. Apoptotic and necrotic cells both represent dead cells.

The cell mixture was cultured on the micro-molds until cluster formation occurred. Clusters were also created using only BMSCs as a control. Media was changed every 24-48 hours while incubating at 37° C. and 5% $CO_2$. Viability was measured. There was approximately 50% viability in cell clusters created only from MSC with the majority of cell death due to apoptosis (FIG. 13). However, when BMSCs were combined with islet cells prior to loading into the micro-mold, then the viability of all of the cells, including the BMSCs, improved to approximately 97% (FIG. 13). It is believed that this self-directed assembly that leads to cluster formation also increases the ability of the cells to arrange according to their respective needs and avoid apoptosis.

Figure 14:
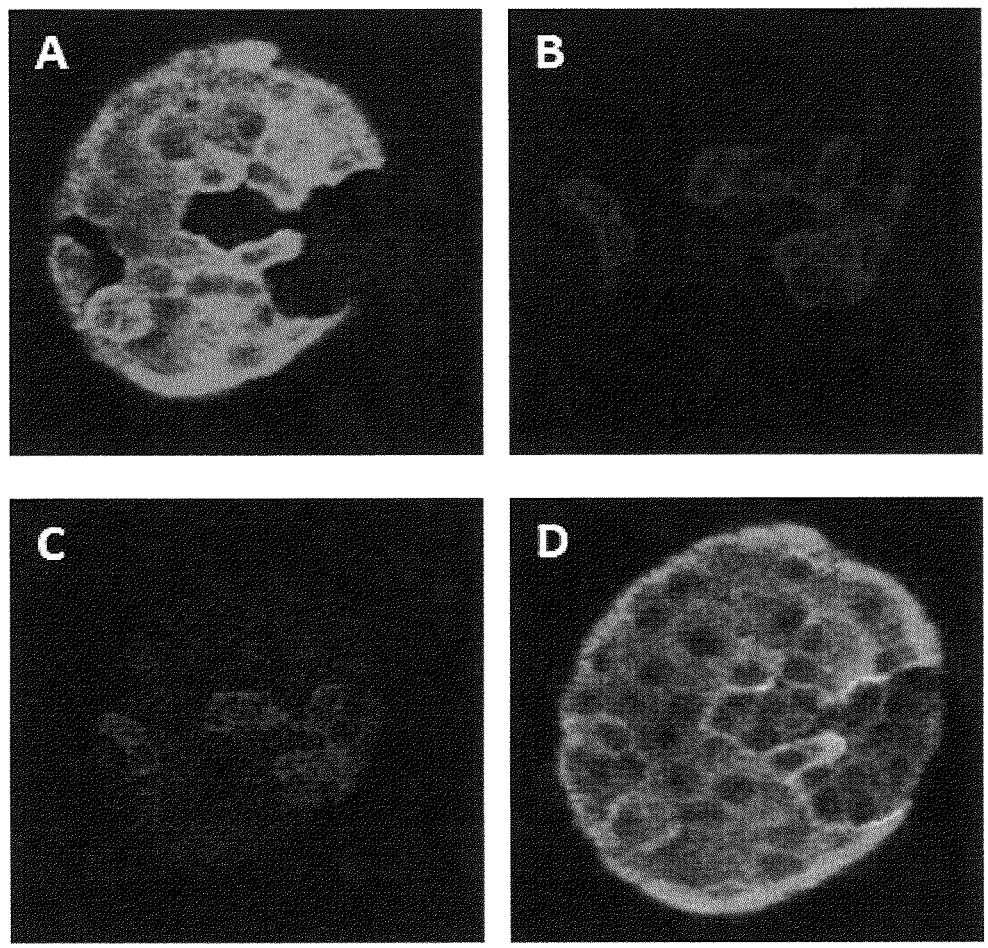
FIG. 14 shows immunofluorescence images of hybrid clusters stained for β cells (A, green), α (B, blue), MSCs (C, red) and β, α, MSC cells (D)

In subsequent work, the BMSCs were stained red so that they could be distinguished from other cells in the hybrid clusters. In the example shown in FIG. 14, the BMSCs (stained red) were found distributed throughout the hybrid cluster.

Example 2

Multi-Donor Cell Clusters

Mixed preparations of 3-D cell clusters, each from different donors (FIG. 8, left) have been created from isolated pancreatic islets according to the procedures described in Example 1. The single cell suspensions were then plated onto micro-molds. Within several minutes, cells began to settle into the recesses of the micro-mold and were in close proximity to each other allowing cell-cell re-adhesion. Micro-molds were incubated for 3-5 days at 37° C. and 5% $CO_2$. Aggregate culture medium was changed every 24 to 48 hours until reaggregated islets were formed. The reaggregated clusters were removed by simply washing the micro-mold several times with culture medium until islets dislodged and were aspirated with a pipette. Mixtures of these reaggregated clusters could then be used for testing.

Single cell clusters composed of cells from multiple donors were produced by plating cell mixtures containing cells from 2 or more donors at desired ratios onto the micro-molds. Using the aforementioned techniques, we have created 3-D cell clusters in the shape of spheroids from cells from two different donors. The hybrid spheroids had extremely high viability (over 95% viable cells). In addition, there was no sign of inflammation or cellular rejection of the cells from different donors.

Figure 9:
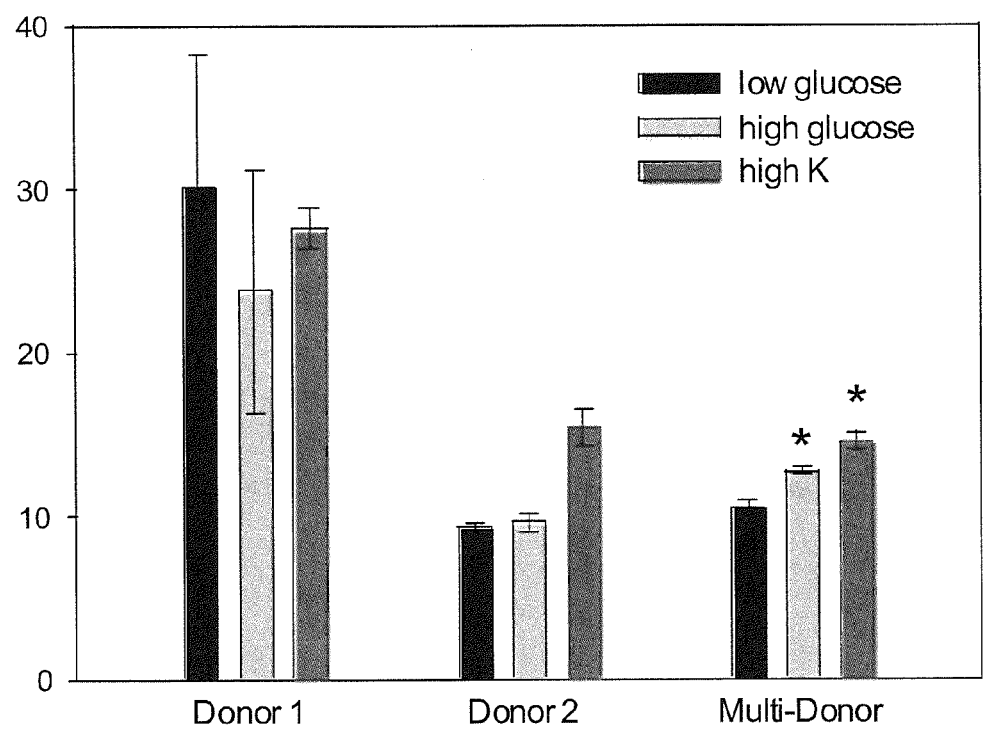
FIG. 9 is a graph of the results from multi-donor islets. Islets from donor 1 dumped large amounts of insulin with no stimulated release to high glucose (17.5 mM) or K+ (20 mM). Donor 2 had no high glucose response. However, when the islets were engineered into uniform multi-donor spheroids, the clusters had a normal response to glucose and high K+ (p<0.001)

The multi-donor engineered islets provide an averaged response to drug testing. FIG. 9 shows the glucose-stimulated release of insulin in native islets from 2 different donors. The data was gathered using a Static Insulin Secretion study. The reaggregated islets were equilibrated overnight in DMEM/F-12 medium containing 5 mM glucose and 10% FBS (low glucose medium). Native islets were used for comparison, and handpicked using a micropipette and a known quantity of islet equivalents were distributed in 24-well plates. The multi-donor engineered islets and native islets were subject to low glucose (5 mM), high glucose (17.5 mM) or high glucose with KCl (20 mM). After 60 minutes of static incubation at 37° C. and 5% $CO_2$, conditioned media samples were collected and frozen at −80° C. The insulin concentration was later quantified using an insulin ELISA kit (Alpco). Native islets from donor 1 dumped a large concentration of insulin into the media, which was not dependent on the glucose or $K^+$ concentration, thus illustrating an abnormal response, even though donor 1 was screened for disease and the islets appeared healthy when received. Native islets from donor 2 released less total insulin, but did show a normal $K^+$-stimulated increase in insulin secretion. However, when the native islets from these two different donors were mixed together and reaggregated using our process into multi-source islets, they now responded to high glucose levels and $K^+$ with normal increases in insulin secretion.

Figure 15:
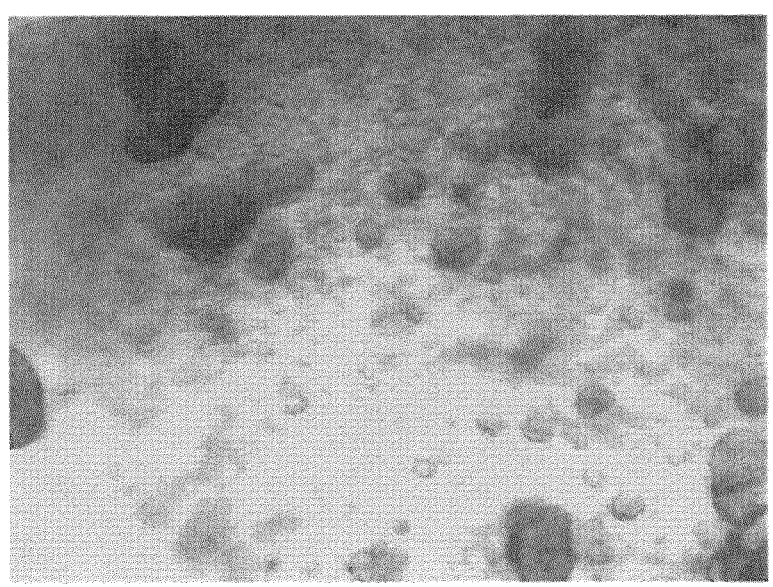
FIG. 15 is an image of decellularized Wharton's Jelly with multi-cell type islet spheroids.

Instead of using the micro-molds, multi-source or multi-donor spheroids could be created by plating the cell mixtures within or attached to a scaffold material. For example, we have created multi-cell type spheroids within decellularlized Wharton's Jelly (FIG. 15).

Example 3

Cryopreservation Techniques

Figure 19:
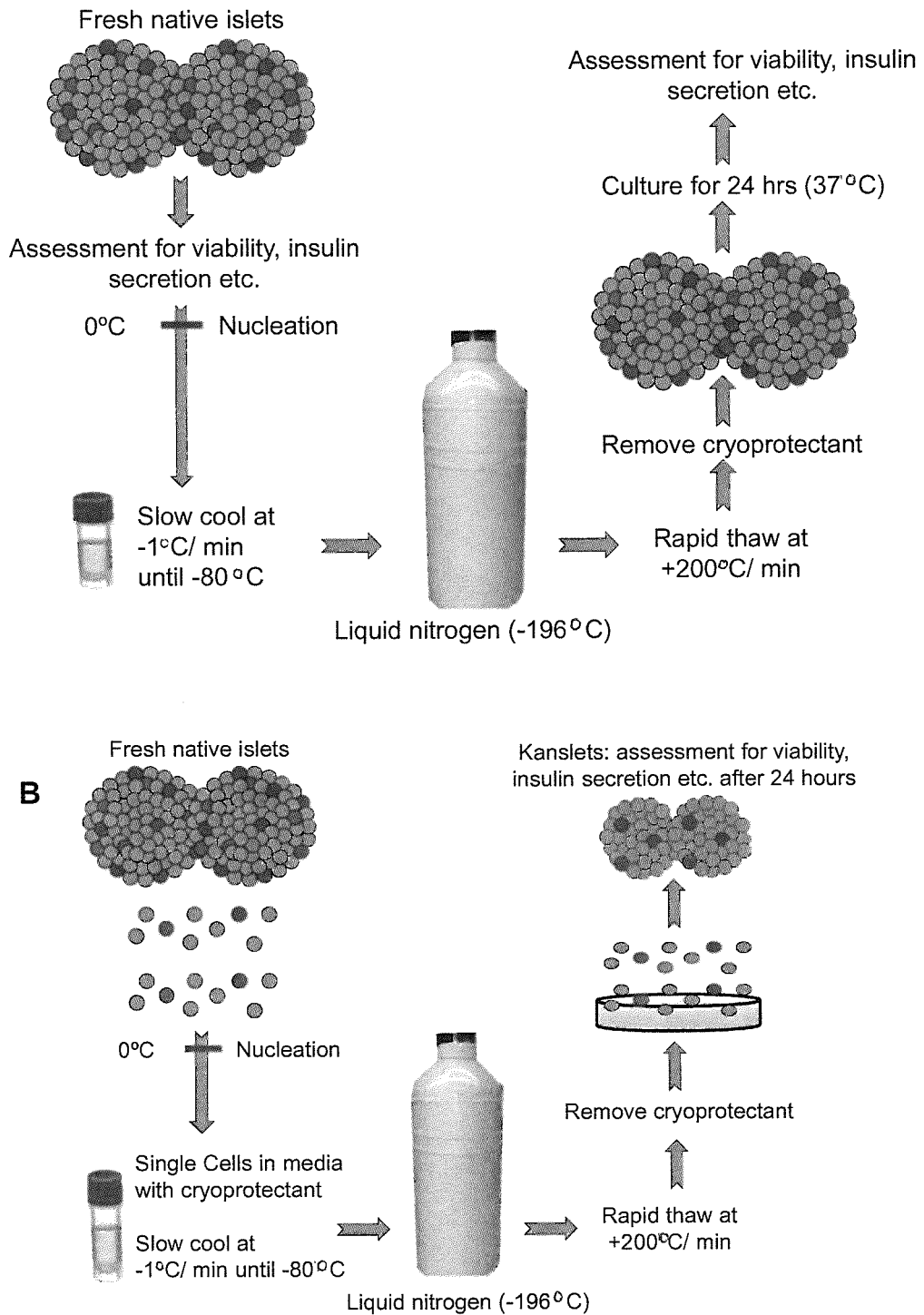
FIG. 19 is an additional illustration of cryopreservation methods, showing the traditional method for cryopreserving intact native islets, and the inventive procedure.

The standard protocol for cryopreservation has been altered to successfully preserve and thaw engineered islets. In addition, improved properties of the engineered islets themselves lend them to improved cryopreservation outcomes. The processes are illustrated in FIG. 19.

In the first protocol, the effect of cryopreservation and thawing was compared between fresh, native islets from human donors and reaggregated islets engineered from human donor islet cells. Engineered Freezing Media was used for the freezing procedure and contains: CMRL-1066 media (Sigma); 1% antibiotic and antimycotic solution; 1% L-glutamine; 16.8 μM/L Zinc Sulfate; 10% Fetal Bovine Serum (FBS); 10 μM Curcumin. The media was buffered with 25 mM HEPES to a final pH of 7.3-7.5.

Before cryopreservation, the engineered islets were maintained overnight at 37° C. in the incubator at 95% air and 5% $CO_2$ in RPMI-1640 (Sigma) medium supplemented with 5 mM/L glucose, 10% fetal bovine serum, 1% antibiotic and antimycotic solution, 1% L-glutamine, 16.8 μM/L zinc sulphate, buffered with 25 Mm/L HEPES. After culturing the engineered islets overnight, they were centrifuged at 2,500 rpm for 5 minutes at 22° C.

The centrifuged pellet was then re-suspended in 200 μL of the Engineered Freezing Media and transferred into a 1.8 mL cryotube, which was kept on ice. Over the next 6 minutes, 100 μL of the Engineered Cryoprotective Solution was added to the cryotube every 1 min. The Engineered Cryoprotective Solution contains 10% DMSO with 10 μM curcumin in CMRL-1066 media. The cryotube was then transferred to a cool cell and kept in the cell in a −80° C. freezer, with controlled freezing at a rate of −1° C./minute. After 8 hours the cryotube was transferred into liquid nitrogen where it is stored until thawing.

For thawing, the cryotube was removed from the liquid nitrogen and the engineered islets were allowed to thaw rapidly to 0° C. As soon as the last ice crystal had disappeared, the tube was centrifuged at 2,500 rpm for 5 min at 4° C. The supernatant was removed and 200 μL of 0.75 M Engineered Sucrose Solution was added every 5 minutes for a period of 30 minutes at 4° C. The Engineered Sucrose Solution contained: CMRL-1066 media; 1% antibiotic and antimycotic solution; 1% L-glutamine; 10% FBS; and 0.75 M sucrose.

Sequential dilution of the Engineered Sucrose Solution was completed by adding 2.5, 2.5, 5.0, and 10.0 mL of Engineered Freezing Media in a stepwise manner over the next 20 minutes. Subsequently, the thawed islets were centrifuged at 2,500 rpm for 5 minutes and the supernatant removed. The engineered islets were resuspended in Engineered Freezing Media and transferred to culture plates where they were maintained at 37° C. in an atmosphere of 95% air and 5% $CO_2$.

The smaller size and lower diffusion barrier of engineered islets as compared to native islets, allowed for the cryopreservation media to penetrate the core of the engineered islet and protect all cells during the freezing process (FIG. 10B). Compared to the core cell death measured in the native islet, the engineered islets survived the cryopreservation procedure much better.

In the second protocol for creating and preserving engineered islets, the tissue is first dispersed into single cells for cryopreservation, instead of cryopreserving the intact islet. This procedure is shown schematically in FIG. 11, and contrasted with the process of cryopreserved whole islets. Native islet tissue is dispersed into single islet cells using the protocols described above. The single islet cells are maintained overnight in RPMI-1640 medium supplemented with 5 mM/L glucose, 10% FBS, 1% antibiotic and antimycotic solution, 1% L-glutamine, 16.8 µM/L zinc sulphate buffered with 25 Mm/L HEPES at 37° C. in the incubator at 95% air and 5% $CO_2$. After culturing the islet cells overnight, they were centrifuged at 2,500 rpm for 5 minutes at 22° C.

The centrifuged pellet was then re-suspended in 200 µL of Cell Freezing Media and transferred into a 1.8 mL cryotube, which was kept on ice. The Cell Freezing Media contained: RPMI-1640 media; 1% antibiotic and antimycotic solution; 1% L-glutamine; 16.8 µM/L Zinc Sulfate; 10% FBS; 10 µM Curcumin; and 5 mM/L glucose. The media was buffered with HEPES to a final pH of 7.3-7.5. Over the next 6 minutes, 100 µL of the Cell Cryoprotective Solution was added to the cryotube every 1 min. The Cell Cryoprotective Solution contained 10% DMSO with 10 µM curcumin in RPMI-1640 media. The cryotube was then transferred to a cool cell and kept in the cell in a −80° C. freezer, with controlled freezing at a rate of −1° C./minute. After 8 hours, the cryotube was transferred to liquid nitrogen, where it was stored until thawing.

The cryotubes were removed from the liquid nitrogen and the islet cells were allowed to thaw rapidly to 0° C. As soon as the last ice crystal had disappeared, the tube was centrifuged at 2,500 rpm for 5 min at 4° C. The supernatant was removed and 200 µL of 0.75 M sucrose solution was added every 5 minutes for a period of 30 minutes at 4° C. The Islet Cell Sucrose Solution contained: RPMI-1640 media; 1% antibiotic and antimycotic solution; 1% L-glutamine; 10% FBS; 5 mM glucose; and 0.75 M sucrose.

Sequential dilution of the Islet Cell Sucrose Solution was completed by adding 2.5, 2.5, 5.0, and 10.0 mL of Islet Cell Freezing Media in a stepwise manner over the next 20 minutes. Subsequently, the cells were centrifuged at 2,500 rpm for 5 minutes and the supernatant was removed. The islet cells were resuspended in Islet Cell Freezing Media and transferred to culture plates or the micro-mold for reaggregation, where they were maintained at 37° C. in an atmosphere of 95% air and 5% $CO_2$.

Figure 16:
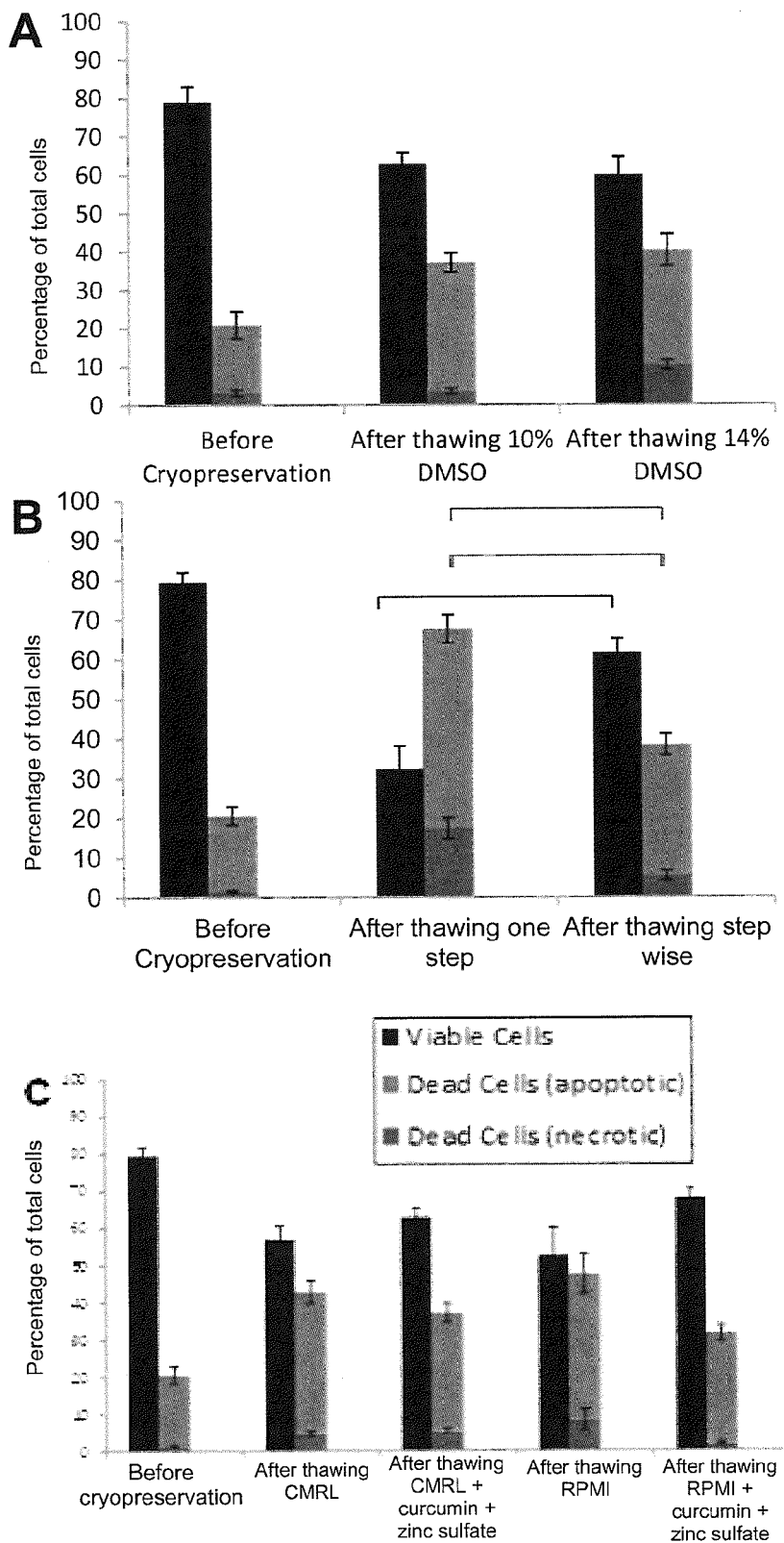
FIG. 16 shows graphs of viable and dead (apoptotic and necrotic) cells after thawing following prolonged cryopreservation. The graphs represent the different protocol alterations that were made to obtain the optimal cryopreservation protocol. A) Different DMSO levels were tried; B) Different equilibration times were tested; and C) Different medias were tested.

Breaking the islets into single cells for freezing removes the diffusion barrier that islets possess that can prevent cryoprotectants from reaching the core of the islet, latent heat of ice crystallization from escaping the core, or a number of other possible issues during the freezing or thawing process. The reaggregation of the islet cells post-cryopreservation allows the viable cells to reaggregate, while any dead cells are left behind. FIG. 16 illustrates some of the different protocols and medias tested to finally produce the optimal cryopreservation protocol that resulted in adequate viability. The described cryopreservation techniques are so improved that there is no statistically significant difference in the percentage of live cells from fresh engineered islets and islets engineered from cryopreserved islet cells (FIG. 17B).

Figure 17:
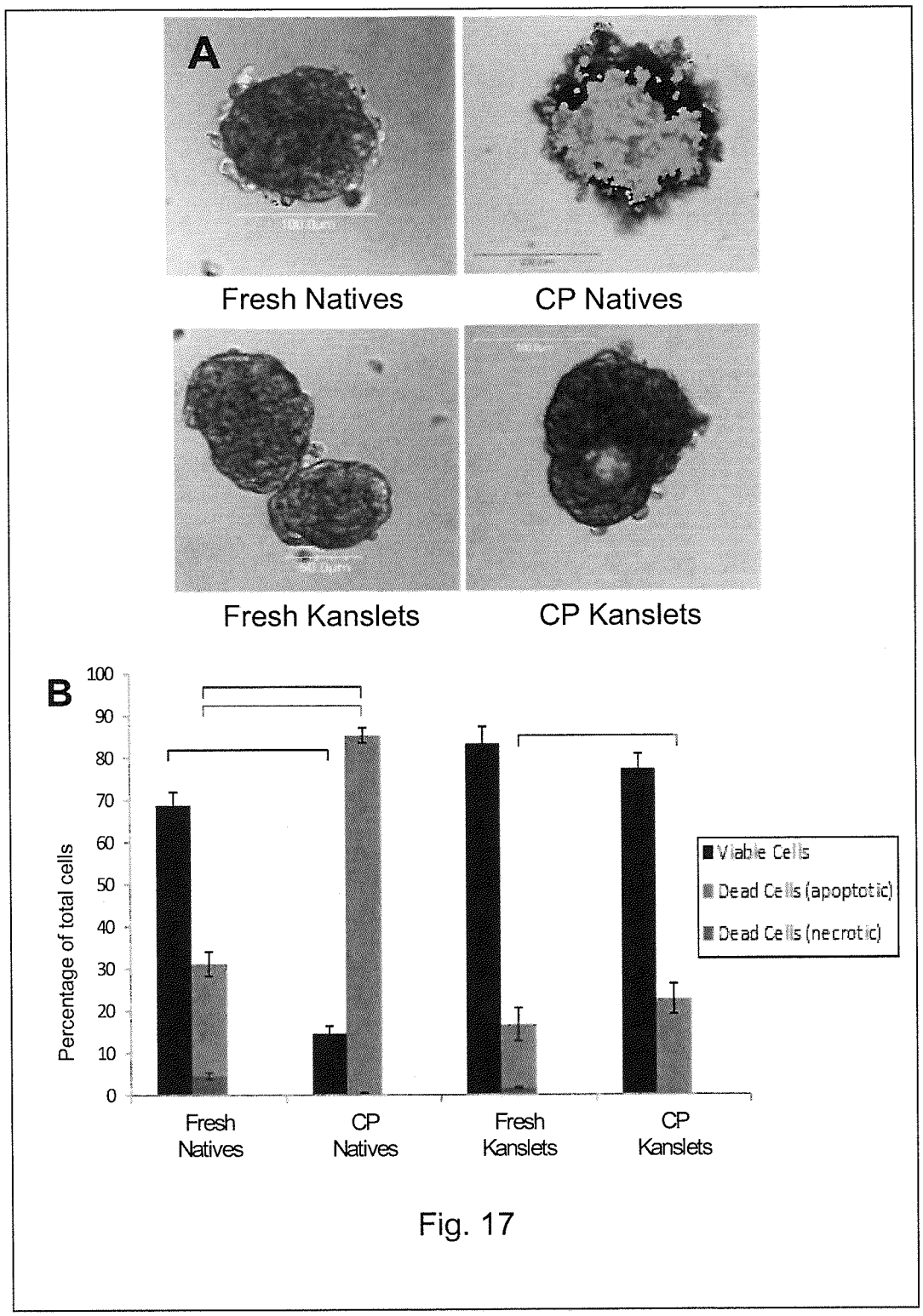
FIG. 17 shows (A) The staining of the cryopreserved native islets for dead cells. The green fluorescent stain is the apoptotic stain; and (B) A graph showing that there is no statistically significant difference in the percentage of live cells between the fresh and cryopreserved (CP) Kanslets.
Figure 18:
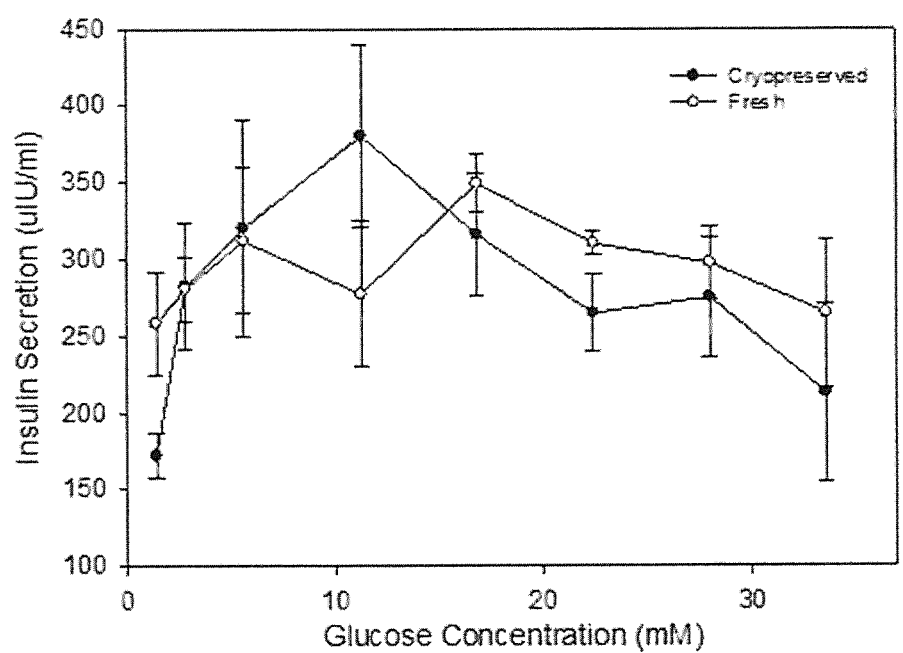
FIG. 18 show a graph indicating that the fresh Kanslets respond appropriately to increasing doses of glucose, and after cryopreservation and thawing, the Kanslets from the same donor responded in an equivalent manner.

A direct comparison of the changes measured in viability after cryopreservation of native islets versus cryopreservation of engineered islets using the method described here is shown in FIG. 17. There is a dramatic increase in the cell death after cryopreservation of native islets that is mainly due to apoptosis, but this shift is not noted after cryopreservation of engineered islets, using the methods described here. FIG. 18 shows that the islet cells respond to a midrange concentration of islets, but fail to respond further when the glucose concentration is too high (hyperphysiological). This is normal in fresh tissue (FIG. 18, open bars), and is maintained after cryopreservation.

What is claimed:

1. A 3-dimensional cluster of reaggregated cells comprising islet cells reaggregated from at least two different donors.

2. The 3-dimensional cluster of claim 1, wherein said individual cell cluster further comprises at least two different cell types.

3. The 3-dimensional cluster of claim 1, wherein said donors are different genders, genotypes, ages, races, ethnic groups, enzymatic or metabolic activities, species, or disease or health states.

4. The 3-dimensional cluster of claim 1, wherein each of said donors are of the same species, sub-species, gender, race, ethnic group, age, geographic region, disease state, or body mass index.

5. A method of forming a 3-dimensional cluster of reaggregated cells according to claim 1, said method comprising:
providing a micro-mold comprising a non-adherent, divoted substrate comprising a substantially planar top surface, wherein the substantially planar top surface comprises a plurality of divots formed therein;
providing single islet cells from at least two different donors;
introducing said single islet cells into said divots, wherein each divot contains a mixture of single islet cells from at least two different donors; and
incubating said micro-mold under cell culture conditions, wherein said single islet cells in each divot reaggregate into a 3-dimensional cell cluster comprising islet cells reaggregated from said at least two different cell donors.

6. The method of claim 5, wherein said providing single islet cells from at least two different donors comprises dispersing islets from at least two different donors into single islet cells.

7. The method of claim 5, wherein said introducing comprises:
mixing said single islet cells from at least two different donors to create a mixture of single islet cells from at least two different donors; and
loading said mixture of single islet cells onto said micro-mold as one aliquot, wherein said mixture of single islet cells settle into respective divots, wherein each divot contains a mixture of single islet cells from at least two different donors.

8. The method of claim 5, wherein said introducing comprises sequentially introducing said single islet cells from a first donor into said divots; and introducing said single islet cells from a second donor different from said first donor into said divots, wherein each divot contains a mixture of single islet cells from at least two different donors.

* * * * *